US 11,701,464 B2

United States Patent
Yosef et al.

(10) Patent No.: US 11,701,464 B2
(45) Date of Patent: Jul. 18, 2023

(54) DRAWING DRUG FROM A VIAL

(71) Applicant: EITAN MEDICAL LTD., Netanya (IL)

(72) Inventors: Andrei Yosef, Even Yehuda (IL); Shaul Eitan, Hofit (IL); Boaz Eitan, Hofit (IL); Ori Ben-David, Tel-Aviv (IL)

(73) Assignee: EITAN MEDICAL LTD., Netanya (IL)

(*) Notice: Subject to any disclaimer, the term of this patent is extended or adjusted under 35 U.S.C. 154(b) by 508 days.

(21) Appl. No.: 16/936,471

(22) Filed: Jul. 23, 2020

(65) Prior Publication Data

US 2020/0353159 A1  Nov. 12, 2020

Related U.S. Application Data

(63) Continuation of application No. 16/591,848, filed on Oct. 3, 2019, now Pat. No. 11,357,909.

(Continued)

(51) Int. Cl.
*A61M 5/142* (2006.01)
*A61M 5/162* (2006.01)
(Continued)

(52) U.S. Cl.
CPC ........ *A61M 5/14216* (2013.01); *A61M 5/162* (2013.01); *A61M 5/172* (2013.01);
(Continued)

(58) Field of Classification Search
CPC .. A61M 5/14216; A61M 5/162; A61M 5/172; A61M 2005/1583;
(Continued)

(56) References Cited

U.S. PATENT DOCUMENTS 3,464,359 A  9/1969  King et al.
3,469,578 A  9/1969  Bierman
(Continued)

FOREIGN PATENT DOCUMENTS

EP  0223451  5/1987
EP  0268480  5/1988
(Continued)

OTHER PUBLICATIONS

An Office Action dated Dec. 3, 2021, which issued during the prosecution of U.S. Appl. No. 16/591,848.
(Continued)

*Primary Examiner* — James D Ponton
(74) *Attorney, Agent, or Firm* — Sughrue Mion, PLLC

(57) ABSTRACT

A substance delivery device engages with a reservoir, and includes a pump that draws therapeutic substance from the reservoir into a pump chamber of the delivery device without changing the internal dimensions of the reservoir. The volume of the therapeutic substance within the pump chamber varies in response to changes in the internal dimensions of the pump chamber. An orientation sensor generates an output indicating an orientation of the delivery device with respect to gravity. Control circuitry drives the pump to: calculate a volume of the substance within the reservoir, draw the substance into the pump chamber in response to (i) the calculated volume, in combination with (ii) an output from the orientation sensor that the delivery device is in an orientation that allows the substance to be drawn from the reservoir, and deliver the substance from the pump chamber to the subject. Other applications are also described.

20 Claims, 20 Drawing Sheets

Related U.S. Application Data

(60) Provisional application No. 62/805,021, filed on Feb. 13, 2019, provisional application No. 62/741,572, filed on Oct. 5, 2018.

(51) Int. Cl.
  *A61M 5/172* (2006.01)
  *A61M 5/158* (2006.01)

(52) U.S. Cl.
  CPC ............... *A61M 2005/1583* (2013.01); *A61M 2005/1585* (2013.01)

(58) Field of Classification Search
  CPC .. A61M 2005/1585; A61M 2005/1425; A61M 5/14546; A61M 2005/14573; A61M 5/24; A61M 2005/2403; A61M 2005/2407; A61M 2005/2411; A61M 2005/2414; A61M 5/14248; A61M 2005/14264; A61M 2005/14268
  See application file for complete search history.

(56) References Cited

U.S. PATENT DOCUMENTS

| | | |
|---|---|---|
| 3,993,061 A | 11/1976 | O'Leary |
| 4,511,355 A | 4/1985 | Franetzki et al. |
| 4,585,435 A | 4/1986 | Vaillancourt |
| 4,909,790 A | 3/1990 | Tsujikawa et al. |
| 4,968,301 A | 11/1990 | Di Palma et al. |
| 5,085,656 A | 2/1992 | Polaschegg |
| 5,129,884 A | 7/1992 | Dysarz |
| 5,178,610 A | 1/1993 | Tsujikawa et al. |
| 5,207,645 A | 5/1993 | Ross et al. |
| 5,242,406 A | 9/1993 | Gross et al. |
| 5,242,411 A | 9/1993 | Yamamoto et al. |
| 5,279,558 A | 1/1994 | Kriesel et al. |
| 5,324,258 A | 6/1994 | Rohrbough |
| 5,439,355 A | 8/1995 | Jimison et al. |
| 5,450,847 A | 9/1995 | Kampfe et al. |
| 5,708,367 A | 1/1998 | Tousson |
| 5,785,688 A | 7/1998 | Joshi et al. |
| 5,814,020 A | 9/1998 | Gross |
| 5,897,530 A | 4/1999 | Jackson |
| 5,919,167 A | 7/1999 | Mulhauser et al. |
| 5,993,423 A | 11/1999 | Choi |
| 6,086,561 A | 7/2000 | Kriesel |
| 6,146,109 A | 11/2000 | Davis et al. |
| 6,171,276 B1 | 1/2001 | Lippe et al. |
| 6,186,982 B1 | 2/2001 | Gross et al. |
| 6,227,807 B1 | 5/2001 | Chase |
| 6,248,093 B1 | 6/2001 | Moberg |
| 6,293,159 B1 | 9/2001 | Kriesel et al. |
| 6,362,591 B1 | 3/2002 | Moberg |
| 6,468,261 B1 | 10/2002 | Small et al. |
| 6,485,461 B1 | 11/2002 | Mason et al. |
| 6,485,465 B2 | 11/2002 | Moberg et al. |
| 6,530,217 B1 | 3/2003 | Yokota et al. |
| 6,530,900 B1 | 3/2003 | Daily et al. |
| 6,542,350 B1 | 4/2003 | Rogers |
| 6,555,986 B2 | 4/2003 | Moberg |
| 6,645,171 B1 | 11/2003 | Robinson et al. |
| 6,656,158 B2 | 12/2003 | Mahoney et al. |
| 6,656,159 B2 | 12/2003 | Flaherty |
| 6,659,980 B2 | 12/2003 | Moberg et al. |
| 6,669,669 B2 | 12/2003 | Flaherty et al. |
| 6,673,035 B1 | 1/2004 | Rice et al. |
| 6,680,597 B1 | 1/2004 | Catellani et al. |
| 6,699,218 B2 | 3/2004 | Flaherty et al. |
| 6,740,059 B2 | 5/2004 | Flaherty |
| 6,749,403 B2 | 6/2004 | Bryant et al. |
| 6,853,160 B1 | 2/2005 | Gandel et al. |
| 6,979,316 B1 | 12/2005 | Rubin et al. |
| 7,029,455 B2 | 4/2006 | Flaherty |
| 7,052,251 B2 | 5/2006 | Nason et al. |
| 7,115,108 B2 | 10/2006 | Wilkinson et al. |
| 7,137,964 B2 | 11/2006 | Flaherty |
| 7,144,384 B2 | 12/2006 | Gorman et al. |
| 7,255,690 B2 | 8/2007 | Gray et al. |
| 7,278,981 B2 | 10/2007 | Ellingboe et al. |
| 7,303,549 B2 | 12/2007 | Flaherty et al. |
| 7,390,314 B2 | 6/2008 | Stutz, Jr. et al. |
| 7,442,186 B2 | 10/2008 | Blomquist |
| 7,455,664 B2 | 11/2008 | Fleury et al. |
| 7,466,092 B2 | 12/2008 | Prudham |
| 7,470,258 B2 | 12/2008 | Barker et al. |
| 7,503,278 B2 | 3/2009 | Sigg et al. |
| 7,510,548 B2 | 3/2009 | Fangrow |
| 7,524,304 B2 | 4/2009 | Genosar |
| 7,530,964 B2 | 5/2009 | Lavi et al. |
| 7,556,623 B2 | 7/2009 | Lyman et al. |
| 7,591,448 B2 | 9/2009 | Martin et al. |
| 7,597,682 B2 | 10/2009 | Moberg |
| 7,621,893 B2 | 11/2009 | Moberg et al. |
| 7,682,338 B2 | 3/2010 | Griffin |
| 7,736,338 B2 | 6/2010 | Kavazov et al. |
| 7,740,619 B2 | 6/2010 | Pinedjian et al. |
| 7,766,873 B2 | 8/2010 | Moberg et al. |
| 7,771,412 B2 | 8/2010 | Anderson et al. |
| 7,887,505 B2 | 2/2011 | Flaherty |
| 7,892,206 B2 | 2/2011 | Moberg et al. |
| 7,918,825 B2 | 4/2011 | O'connor et al. |
| 7,918,843 B2 | 4/2011 | Genosar et al. |
| 7,931,643 B2 | 4/2011 | Olsen et al. |
| 7,937,831 B2 | 5/2011 | Sigg et al. |
| 7,976,505 B2 | 7/2011 | Hines et al. |
| 7,981,085 B2 | 7/2011 | Ethelfeld |
| 8,062,253 B2 | 11/2011 | Nielsen et al. |
| 8,062,257 B2 | 11/2011 | Moberg et al. |
| 8,065,096 B2 | 11/2011 | Moberg et al. |
| 8,072,209 B2 | 12/2011 | Jerance et al. |
| 8,081,069 B2 | 12/2011 | Haueter et al. |
| 8,088,096 B2 | 1/2012 | Lauchard et al. |
| 8,105,280 B2 | 1/2012 | Iddan et al. |
| 8,128,597 B2 | 3/2012 | Cross et al. |
| 8,129,474 B2 | 3/2012 | Ohbi |
| 8,140,275 B2 | 3/2012 | Campbell et al. |
| 8,152,779 B2 | 4/2012 | Cabin et al. |
| 8,172,804 B2 | 5/2012 | Bikovsky |
| 8,182,447 B2 | 5/2012 | Moberg et al. |
| 8,202,250 B2 | 6/2012 | Stutz, Jr. |
| 8,222,777 B2 | 7/2012 | Loussert et al. |
| 8,226,610 B2 | 7/2012 | Edwards et al. |
| 8,231,572 B2 | 7/2012 | Carter et al. |
| 8,246,573 B2 | 8/2012 | Ali et al. |
| 8,267,893 B2 | 9/2012 | Moberg et al. |
| 8,281,656 B2 | 10/2012 | Schnidrig |
| 8,285,328 B2 | 10/2012 | Caffey et al. |
| 8,294,561 B2 | 10/2012 | Strahm et al. |
| 8,298,171 B2 | 10/2012 | Ishikawa et al. |
| 8,303,535 B2 | 11/2012 | Both et al. |
| 8,323,237 B2 | 12/2012 | Radmer et al. |
| 8,347,807 B2 | 1/2013 | Sigg et al. |
| 8,356,645 B2 | 1/2013 | Chong et al. |
| 8,361,031 B2 | 1/2013 | Halbert et al. |
| 8,372,045 B2 | 2/2013 | Needle et al. |
| 8,427,095 B2 | 4/2013 | Bilat et al. |
| 8,435,214 B2 | 5/2013 | Gray et al. |
| 8,444,592 B2 | 5/2013 | Williams et al. |
| 8,449,502 B2 | 5/2013 | Pratt et al. |
| 8,465,468 B1 | 6/2013 | Pettis et al. |
| 8,467,980 B2 | 6/2013 | Campbell et al. |
| 8,480,622 B2 | 7/2013 | Kawamura |
| 8,480,645 B1 | 7/2013 | Choudhury et al. |
| 8,483,980 B2 | 7/2013 | Moberg et al. |
| 8,486,018 B2 | 7/2013 | Kamen et al. |
| 8,502,426 B2 | 8/2013 | Loussert et al. |
| 8,523,803 B1 | 9/2013 | Favreau |
| 8,603,026 B2 | 12/2013 | Favreau |
| 8,603,027 B2 | 12/2013 | Favreau |
| 8,617,110 B2 | 12/2013 | Moberg et al. |
| 8,636,696 B2 | 1/2014 | Ross et al. |
| 8,647,074 B2 | 2/2014 | Moberg et al. |
| 8,647,296 B2 | 2/2014 | Moberg et al. |

(56) References Cited

U.S. PATENT DOCUMENTS

| | | |
|---|---|---|
| 8,668,672 B2 | 3/2014 | Moberg et al. |
| 8,681,010 B2 | 3/2014 | Moberg et al. |
| 8,702,656 B2 | 4/2014 | Kamen et al. |
| 8,708,959 B2 | 4/2014 | Haase |
| 8,708,994 B2 | 4/2014 | Pettis et al. |
| 8,729,912 B2 | 5/2014 | Cefai et al. |
| 8,752,570 B2 | 6/2014 | Donahue |
| 8,784,403 B2 | 7/2014 | Cefai et al. |
| 8,795,234 B2 | 8/2014 | Kadamus et al. |
| 8,808,269 B2 | 8/2014 | Bazargan et al. |
| 8,821,432 B2 | 9/2014 | Unverdorben |
| 8,834,420 B2 | 9/2014 | Estes et al. |
| 8,834,454 B2 | 9/2014 | Genosar et al. |
| 8,858,511 B2 | 10/2014 | Gonnelli et al. |
| 8,864,739 B2 | 10/2014 | Moberg et al. |
| 8,890,380 B2 | 11/2014 | Andrieux et al. |
| 8,894,612 B2 | 11/2014 | Hawkins et al. |
| 8,900,188 B2 | 12/2014 | Blumberg, Jr. et al. |
| 8,905,966 B2 | 12/2014 | Yoh et al. |
| 8,905,970 B2 | 12/2014 | Bates et al. |
| 8,920,367 B2 | 12/2014 | Edwards et al. |
| 8,920,376 B2 | 12/2014 | Caffey et al. |
| 8,920,386 B2 | 12/2014 | Cefai et al. |
| 8,957,674 B2 | 2/2015 | Genoud et al. |
| 8,970,384 B2 | 3/2015 | Yodfat et al. |
| 8,998,850 B2 | 4/2015 | Kamen et al. |
| 8,998,851 B2 | 4/2015 | Constantineau et al. |
| 9,011,371 B2 | 4/2015 | Moberg et al. |
| 9,033,925 B2 | 5/2015 | Moberg et al. |
| 9,050,406 B2 | 6/2015 | Kow et al. |
| 9,061,097 B2 | 6/2015 | Holt et al. |
| 9,089,474 B2 | 7/2015 | Cederschiöld |
| 9,089,637 B2 | 7/2015 | Chong et al. |
| 9,089,641 B2 | 7/2015 | Kavazov |
| 9,107,998 B2 | 8/2015 | Pratt et al. |
| 9,107,999 B2 | 8/2015 | Moberg et al. |
| 9,180,244 B2 | 11/2015 | Anderson et al. |
| 9,227,010 B2 | 1/2016 | Neta et al. |
| 9,227,019 B2 | 1/2016 | Swift et al. |
| 9,238,112 B2 | 1/2016 | Schoonmaker et al. |
| 9,242,052 B2 | 1/2016 | Pettis et al. |
| 9,250,111 B2 | 2/2016 | Whalley et al. |
| 9,283,322 B2 | 3/2016 | Shih et al. |
| 9,289,551 B2 | 3/2016 | Hata et al. |
| 9,327,073 B2 | 5/2016 | Moberg et al. |
| 9,333,297 B2 | 5/2016 | Li et al. |
| 9,344,024 B2 | 5/2016 | Favreau |
| 9,364,608 B2 | 6/2016 | Moberg et al. |
| 9,379,652 B2 | 6/2016 | Favreau |
| 9,379,653 B2 | 6/2016 | Favreau |
| 9,381,299 B2 | 7/2016 | Kuo et al. |
| 9,402,950 B2 | 8/2016 | Diianni et al. |
| 9,402,951 B2 | 8/2016 | Geipel et al. |
| 9,415,158 B2 | 8/2016 | Miller et al. |
| 9,433,732 B2 | 9/2016 | Moberg et al. |
| 9,433,733 B2 | 9/2016 | Moberg et al. |
| 9,446,185 B2 | 9/2016 | Yodfat et al. |
| 9,452,261 B2 | 9/2016 | Alon |
| 9,463,280 B2 | 10/2016 | Cabin et al. |
| 9,474,857 B2 | 10/2016 | Riley et al. |
| 9,480,624 B2 | 11/2016 | Holt et al. |
| 9,492,613 B2 | 11/2016 | Kamen et al. |
| 9,492,614 B2 | 11/2016 | Kamen et al. |
| 9,498,587 B2 | 11/2016 | Gray |
| 9,504,785 B2 | 11/2016 | Forsell et al. |
| 9,545,474 B2 | 1/2017 | Hanson et al. |
| 9,592,336 B2 | 3/2017 | Nielsen et al. |
| 9,615,997 B2 | 4/2017 | Fangrow |
| 9,616,171 B2 | 4/2017 | Qin et al. |
| 9,623,174 B2 | 4/2017 | Pang et al. |
| 9,636,451 B2 | 5/2017 | Gonnelli et al. |
| 9,649,433 B2 | 5/2017 | Lanier, Jr. et al. |
| 9,662,271 B2 | 5/2017 | Holt et al. |
| 9,662,272 B2 | 5/2017 | Warren et al. |
| 9,677,555 B2 | 6/2017 | Kamen et al. |
| 9,687,186 B2 | 6/2017 | Goldstein et al. |
| 9,717,857 B2 | 8/2017 | Lanier |
| 9,724,462 B2 | 8/2017 | Rotem |
| 9,744,297 B2 | 8/2017 | Cabiri et al. |
| 9,744,304 B2 | 8/2017 | Swift et al. |
| 9,750,871 B2 | 9/2017 | Metzmaker et al. |
| 9,750,875 B2 | 9/2017 | Smith et al. |
| 9,750,953 B2 | 9/2017 | Kalafut |
| 9,782,545 B2 | 10/2017 | Gross et al. |
| 9,789,027 B2 | 10/2017 | Sund et al. |
| 9,795,735 B2 | 10/2017 | Levesque et al. |
| 9,812,918 B2 | 11/2017 | Andrieux |
| 9,813,985 B2 | 11/2017 | Shapley et al. |
| 9,821,117 B2 | 11/2017 | Anderson et al. |
| 9,839,737 B2 | 12/2017 | Reiter et al. |
| 9,849,238 B2 | 12/2017 | Li et al. |
| 9,861,769 B2 | 1/2018 | Kamen et al. |
| 9,861,801 B2 | 1/2018 | Baker et al. |
| 9,867,929 B2 | 1/2018 | Searle et al. |
| 9,878,091 B2 | 1/2018 | Cabiri |
| 9,881,367 B1 | 1/2018 | Milne et al. |
| 9,884,151 B2 | 2/2018 | Sullivan et al. |
| 9,889,256 B2 | 2/2018 | Cabin et al. |
| 9,901,672 B2 | 2/2018 | Despa et al. |
| 9,925,333 B2 | 3/2018 | Hooven et al. |
| 9,940,440 B2 | 4/2018 | Ali et al. |
| 9,943,643 B2 | 4/2018 | Constantineau et al. |
| 9,950,110 B2 | 4/2018 | Mandro et al. |
| 9,956,345 B2 | 5/2018 | Anderson et al. |
| 9,974,942 B2 | 5/2018 | Beiriger |
| 9,987,428 B2 | 6/2018 | Tan-malecki et al. |
| 9,999,724 B2 | 6/2018 | Cindrich et al. |
| 10,010,674 B2 | 7/2018 | Rosinko et al. |
| 10,029,046 B2 | 7/2018 | Haueter et al. |
| 10,034,976 B2 | 7/2018 | Vazquez et al. |
| 10,034,977 B2 | 7/2018 | Haueter et al. |
| 10,034,983 B2 | 7/2018 | Haueter et al. |
| 10,071,209 B2 | 9/2018 | Solomon et al. |
| 10,088,660 B2 | 10/2018 | Fradkin et al. |
| 10,092,703 B2 | 10/2018 | Mounce et al. |
| 10,092,706 B2 | 10/2018 | Denzer et al. |
| 10,112,005 B2 | 10/2018 | Rotem et al. |
| 10,124,112 B2 | 11/2018 | Diianni et al. |
| 10,130,758 B2 | 11/2018 | Diianni et al. |
| 10,141,882 B2 | 11/2018 | Favreau |
| 10,143,797 B2 | 12/2018 | Limaye |
| 10,183,156 B2 | 1/2019 | Ross et al. |
| 10,195,342 B2 | 2/2019 | Cole et al. |
| 10,220,147 B2 | 3/2019 | Constantineau et al. |
| 10,228,663 B2 | 3/2019 | Favreau |
| 10,232,108 B2 | 3/2019 | Qi et al. |
| 10,245,377 B2 | 4/2019 | Mclaughlin |
| 10,272,197 B2 | 4/2019 | Shapley et al. |
| 10,272,200 B2 | 4/2019 | Shapley et al. |
| 10,279,129 B2 | 5/2019 | Shay |
| 10,314,967 B2 | 6/2019 | Bates et al. |
| 10,314,976 B2 | 6/2019 | Tan-malecki et al. |
| 10,335,542 B2 | 7/2019 | Rotem |
| 10,342,918 B2 | 7/2019 | Politis et al. |
| 10,342,926 B2 | 7/2019 | Nazzaro et al. |
| 10,363,342 B2 | 7/2019 | Dillon et al. |
| 10,363,372 B2 | 7/2019 | Nazzaro |
| 10,363,374 B2 | 7/2019 | Nazzaro et al. |
| 10,369,274 B2 | 8/2019 | O'Connor et al. |
| 10,391,237 B2 | 8/2019 | Cefai et al. |
| 10,391,239 B2 | 8/2019 | Lorenzen et al. |
| 10,398,854 B2 | 9/2019 | Fenster et al. |
| 10,413,665 B2 | 9/2019 | Rioux et al. |
| 10,420,883 B2 | 9/2019 | Diianni et al. |
| 10,438,696 B2 | 10/2019 | Shapley et al. |
| 10,438,698 B2 | 10/2019 | Pillalamarri et al. |
| 10,441,717 B2 | 10/2019 | Schmid et al. |
| 10,441,723 B2 | 10/2019 | Nazzaro |
| 10,448,885 B2 | 10/2019 | Schmid |
| 10,449,290 B2 | 10/2019 | Shapley et al. |
| 10,478,550 B2 | 11/2019 | Hadvary et al. |
| 10,492,990 B2 | 12/2019 | Mounce et al. |
| 10,561,797 B2 | 2/2020 | Nazzaro et al. |
| 10,569,014 B2 | 2/2020 | Hanson et al. |

(56) References Cited

U.S. PATENT DOCUMENTS

| | | | |
|---|---|---|---|
| 10,625,018 B2 | 4/2020 | Destefano et al. |
| 10,646,652 B2 | 5/2020 | Mccullough et al. |
| 10,668,227 B2 | 6/2020 | Caspers |
| 10,729,852 B2 | 8/2020 | Baker et al. |
| 10,737,024 B2 | 8/2020 | Schmid |
| 10,758,705 B2 | 9/2020 | Glithero et al. |
| 10,765,801 B2 | 9/2020 | Mccullough |
| 10,814,062 B2 | 10/2020 | Gyory |
| 11,052,186 B2 | 7/2021 | Bonnefond et al. |
| 11,109,800 B2 | 9/2021 | Hooven et al. |
| 11,116,893 B2 | 9/2021 | Cabiri et al. |
| 11,129,936 B2 | 9/2021 | Gibson et al. |
| 11,213,624 B2 | 1/2022 | McCullough et al. |
| 2003/0014014 A1 | 1/2003 | Nitzan |
| 2003/0065287 A1 | 4/2003 | Spohn et al. |
| 2003/0109827 A1 | 6/2003 | Lavi et al. |
| 2004/0010207 A1 | 1/2004 | Flaherty et al. |
| 2004/0013538 A1 | 1/2004 | Fuchs |
| 2004/0015042 A1 | 1/2004 | Vincent et al. |
| 2004/0064101 A1 | 4/2004 | Kowan et al. |
| 2004/0162521 A1 | 8/2004 | Bengtsson |
| 2005/0147508 A1 | 7/2005 | Luongo et al. |
| 2005/0203461 A1 | 9/2005 | Flaherty et al. |
| 2008/0051738 A1 | 2/2008 | Griffin |
| 2009/0036867 A1 | 2/2009 | Glejboel et al. |
| 2009/0036868 A1 | 2/2009 | Pinedjian et al. |
| 2009/0254041 A1 | 10/2009 | Krag et al. |
| 2010/0137830 A1 | 6/2010 | Glejboel et al. |
| 2010/0227818 A1 | 9/2010 | Bock et al. |
| 2010/0292632 A1 | 11/2010 | Mulvihill et al. |
| 2011/0230826 A1 | 9/2011 | Yoh et al. |
| 2012/0022499 A1 | 1/2012 | Anderson et al. |
| 2012/0053562 A1 | 3/2012 | Haase |
| 2013/0090633 A1 | 4/2013 | Loeb |
| 2013/0123703 A1* | 5/2013 | Shay ............... A61M 5/1452 604/153 |
| 2013/0177455 A1 | 7/2013 | Kamen et al. |
| 2014/0088554 A1 | 3/2014 | Li et al. |
| 2014/0142508 A1 | 5/2014 | Diianni et al. |
| 2014/0163477 A1 | 6/2014 | Quinn et al. |
| 2014/0214010 A1 | 7/2014 | Kuo et al. |
| 2014/0221925 A1* | 8/2014 | Kondoh ............ A61M 5/31568 604/111 |
| 2014/0276414 A1* | 9/2014 | Baker ..................... A61M 5/20 434/262 |
| 2015/0029816 A1 | 1/2015 | Beyer et al. |
| 2015/0141920 A1 | 5/2015 | O'connor et al. |
| 2016/0000999 A1 | 1/2016 | Focht et al. |
| 2016/0038666 A1 | 2/2016 | Kelly et al. |
| 2016/0158435 A1 | 6/2016 | Wu et al. |
| 2016/0177937 A1 | 6/2016 | Liu et al. |
| 2016/0184516 A1 | 6/2016 | Shih et al. |
| 2016/0213834 A1 | 7/2016 | Brady et al. |
| 2016/0354555 A1 | 12/2016 | Gibson et al. |
| 2016/0369789 A1 | 12/2016 | Alderete |
| 2017/0189609 A1 | 7/2017 | Wei |
| 2017/0281877 A1 | 10/2017 | Marlin et al. |
| 2017/0368269 A1 | 12/2017 | Kondo |
| 2018/0028747 A1 | 2/2018 | Hanson et al. |
| 2018/0085517 A1 | 3/2018 | Laurence et al. |
| 2018/0272072 A1 | 9/2018 | Radmer et al. |
| 2018/0361082 A1 | 12/2018 | Sall et al. |
| 2019/0151544 A1 | 5/2019 | Stonecipher |
| 2019/0351143 A1 | 11/2019 | Egloff et al. |
| 2019/0365985 A1 | 12/2019 | Zidon et al. |
| 2019/0365990 A1 | 12/2019 | Phillips et al. |
| 2019/0365993 A1 | 12/2019 | Staub et al. |
| 2020/0108201 A1 | 4/2020 | Ben-david et al. |
| 2020/0113515 A1 | 4/2020 | O'connor et al. |

FOREIGN PATENT DOCUMENTS

| | | |
|---|---|---|
| EP | 0293958 | 12/1988 |
| EP | 0380862 | 8/1990 |
| EP | 0464761 | 1/1992 |
| EP | 0937477 | 8/1999 |
| EP | 0555007 | 12/1999 |
| EP | 2060284 | 5/2009 |
| EP | 1677729 | 7/2009 |
| EP | 2134388 | 12/2012 |
| EP | 2902052 | 8/2015 |
| EP | 3354303 | 8/2018 |
| EP | 3050585 | 4/2019 |
| GB | 757116 | 9/1956 |
| WO | 2000/069507 | 11/2000 |
| WO | 2007/077255 | 7/2007 |
| WO | 2008/024810 | 2/2008 |
| WO | 2008/107378 | 9/2008 |
| WO | 2008/133702 | 11/2008 |
| WO | 2010/096449 | 8/2010 |
| WO | 2011/133823 | 10/2011 |
| WO | 2012/108955 | 8/2012 |
| WO | 2012/126744 | 9/2012 |
| WO | 2013/184646 | 12/2013 |
| WO | 2014/090745 | 6/2014 |
| WO | 2014/191038 | 12/2014 |
| WO | 2015/032747 | 3/2015 |
| WO | 2015/038556 | 3/2015 |
| WO | 2015/048093 | 4/2015 |
| WO | 2016/164349 | 10/2016 |
| WO | 2017/192287 | 11/2017 |
| WO | 2018/096534 | 5/2018 |
| WO | 2018/141697 | 8/2018 |
| WO | 2019/159121 | 8/2019 |

OTHER PUBLICATIONS

Communication dated Sep. 11, 2020 by the European Patent Office in application No. 20187553.1.
European Search Report dated Oct. 5, 2022 which issued during the prosecution of Applicant's European App No. 22173099.7.
U.S. Appl. No. 61/940,601, filed Feb. 17, 2014.
An International Search Report and a Written Opinion both dated Jan. 19, 2018, which issued during the prosecution of Applicant's PCT/IL2017/051276.
U.S. Appl. No. 62/805,021, filed Feb. 13, 2019.
U.S. Appl. No. 62/741,572, filed Oct. 5, 2018.
European Search Report dated Dec. 12, 2019, which issued during the prosecution of Applicant's European App No. 19201363.9.
An International Search Report and a Written Opinion both dated Jun. 9, 2020, whichissued during the prosecution of PCT/IL2020/050246.
ManagerSonceboz, T. (Sep. 2018). Drug Delivery Meets Automotive Engineering. Retrieved Aug. 10, 2020, from https://www.ondrugdelivery.com/drug-delivery-meets-automotive-engineering/.
LYCAJECT: Automatic Reconstitution Patch Injector. (Feb. 2019). Retrieved Aug. 10, 2020, from https://www.ondrugdelivery.com/lycaject-automatic-reconstitution-patch-injector/.
An Office Action dated Aug. 3, 2021, which issued during the prosecution of U.S. Appl. No. 16/462,458.
An Office Action dated Feb. 9, 2023, which issued during the prosecution of European Patent Application No. 19201363.9.

* cited by examiner

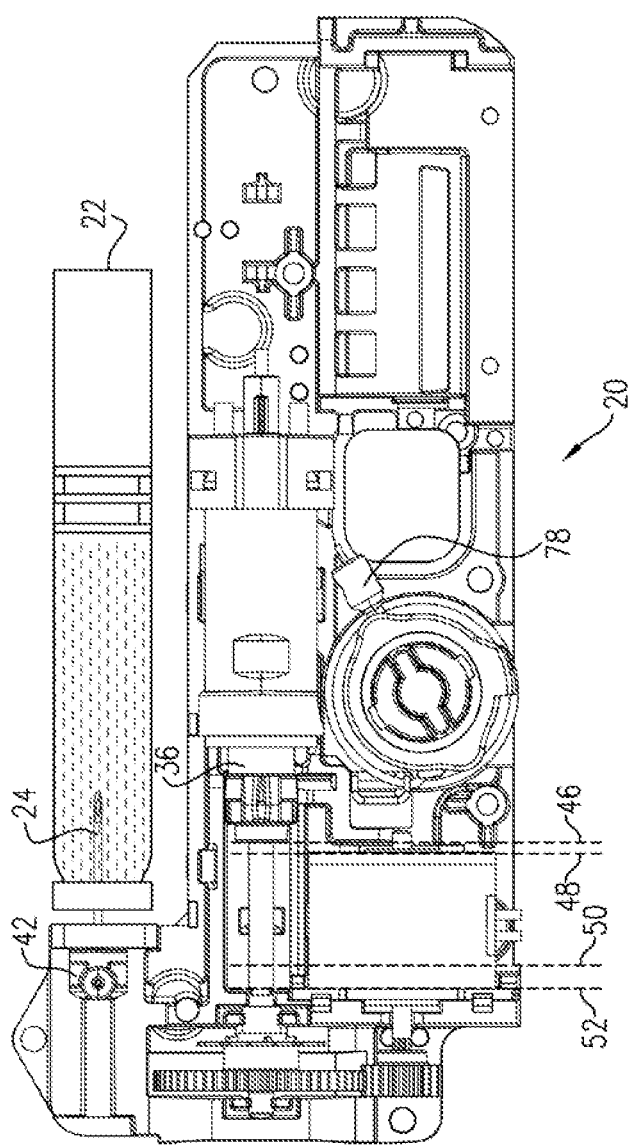
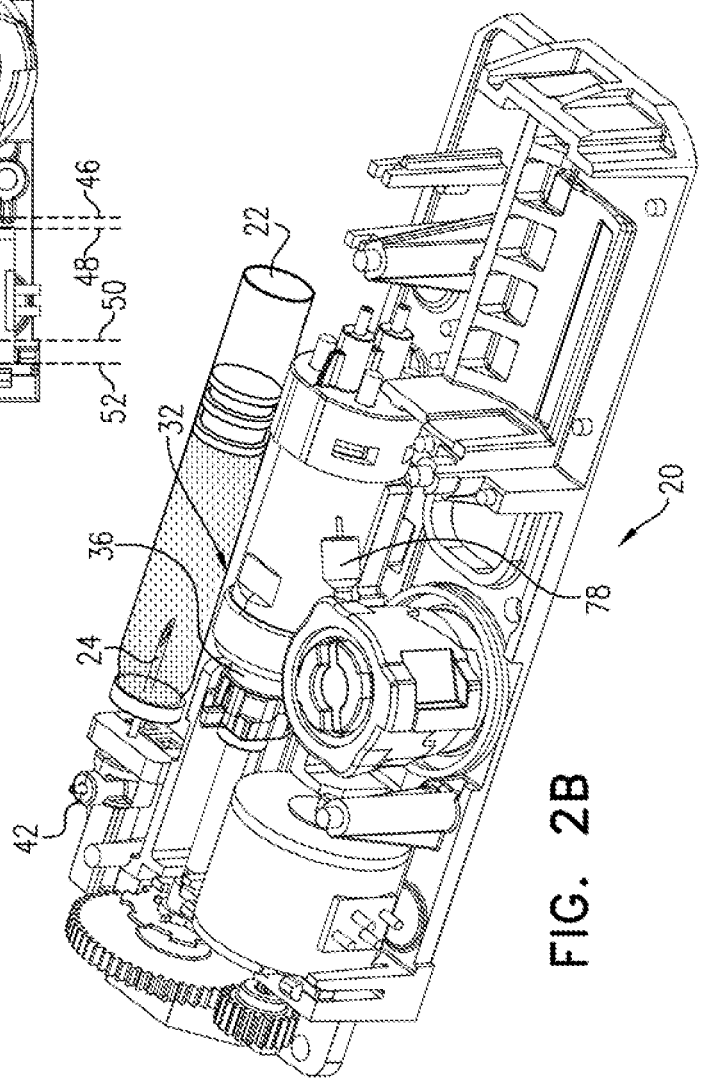
FIG. 2A
FIG. 2B

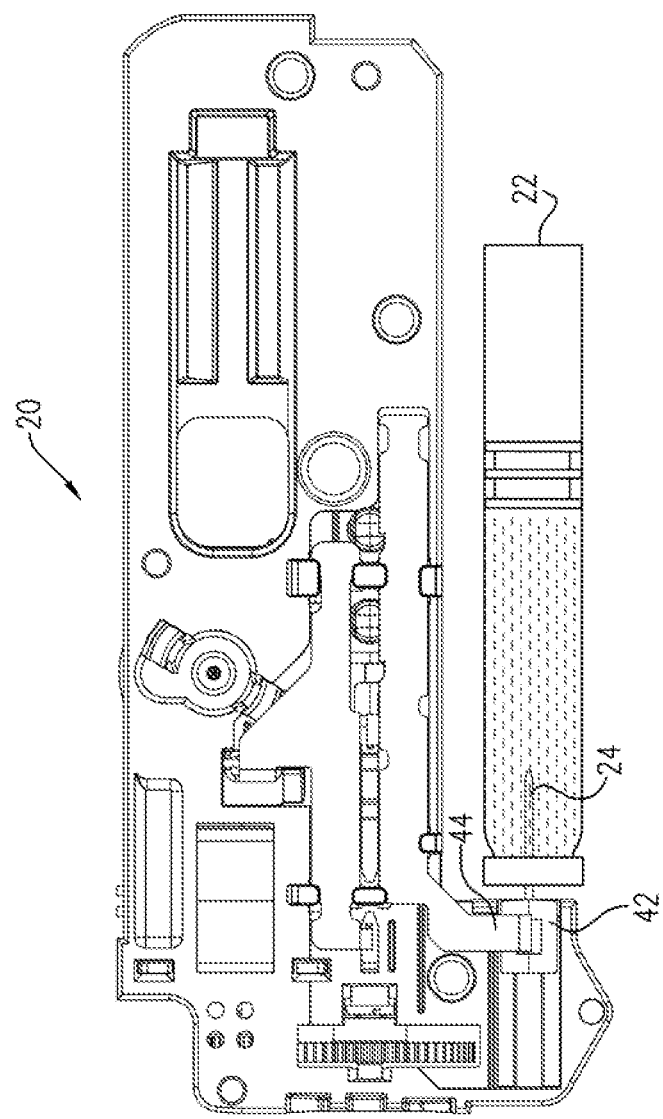

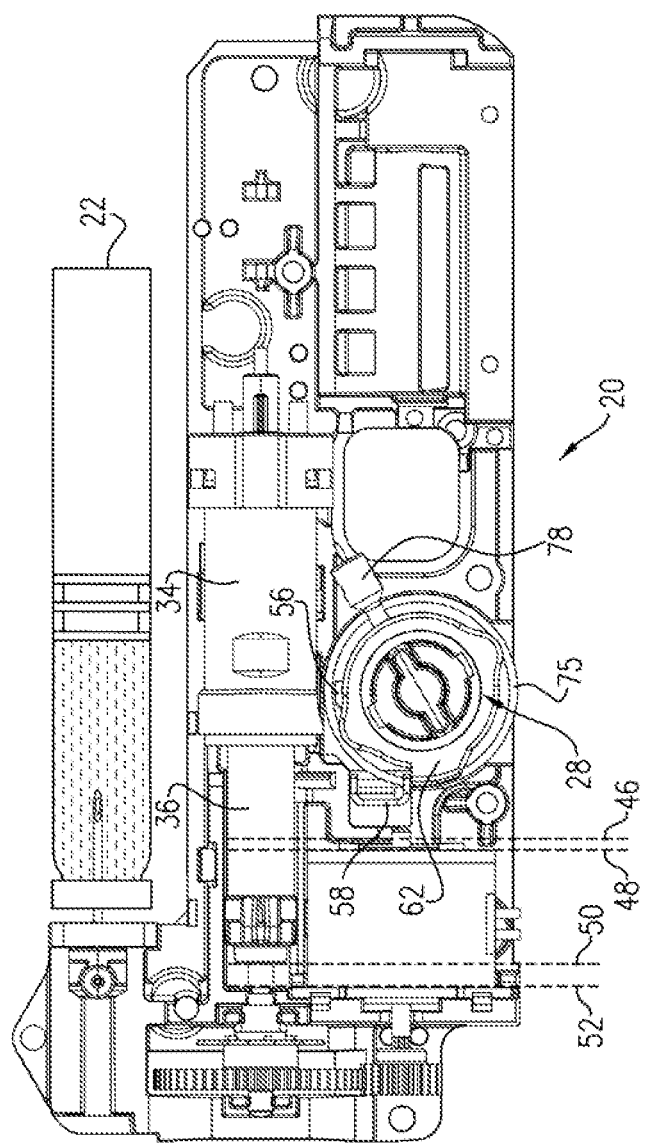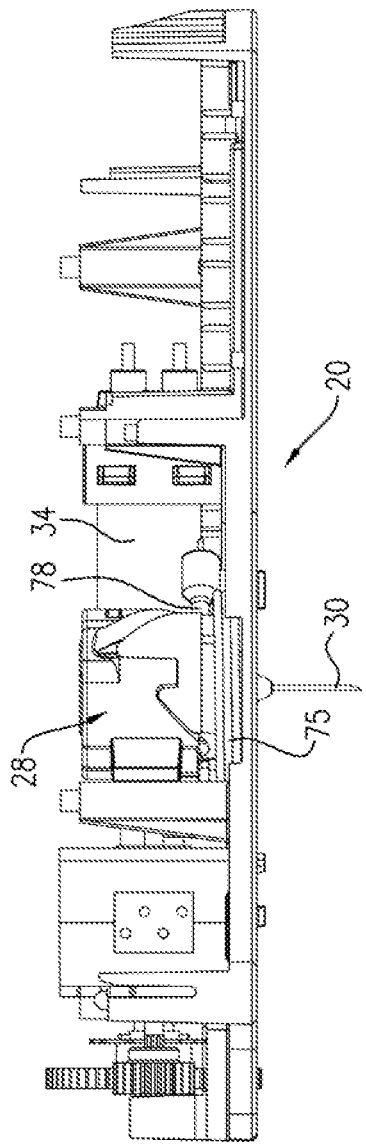
FIG. 3A
FIG. 3B

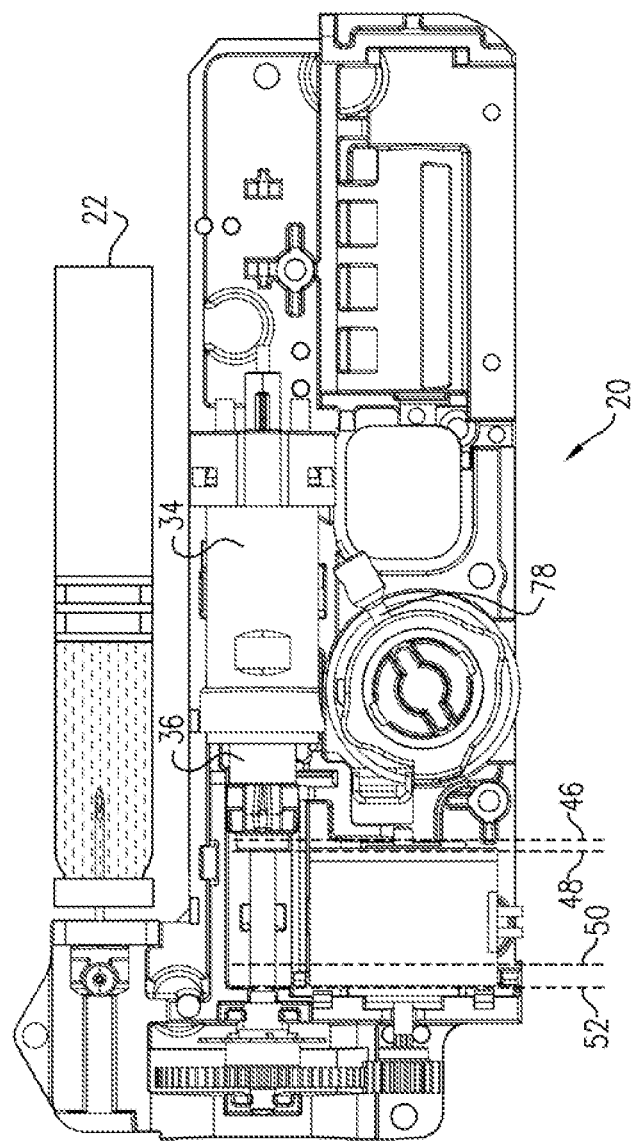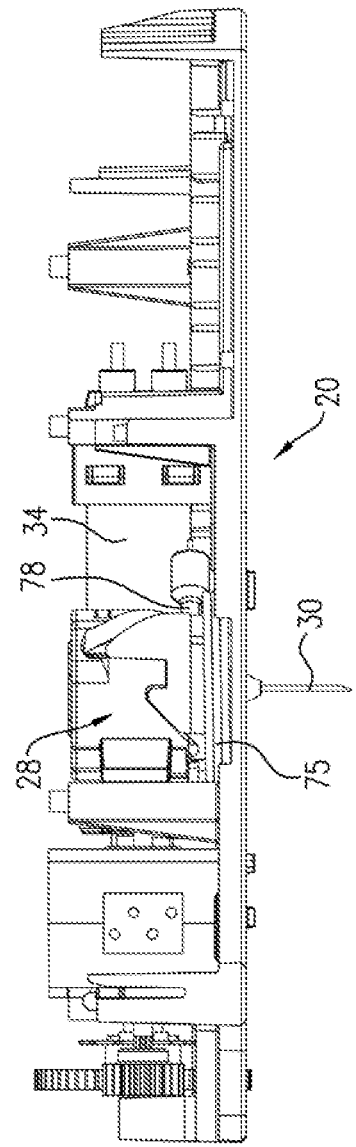
FIG. 4A
FIG. 4B

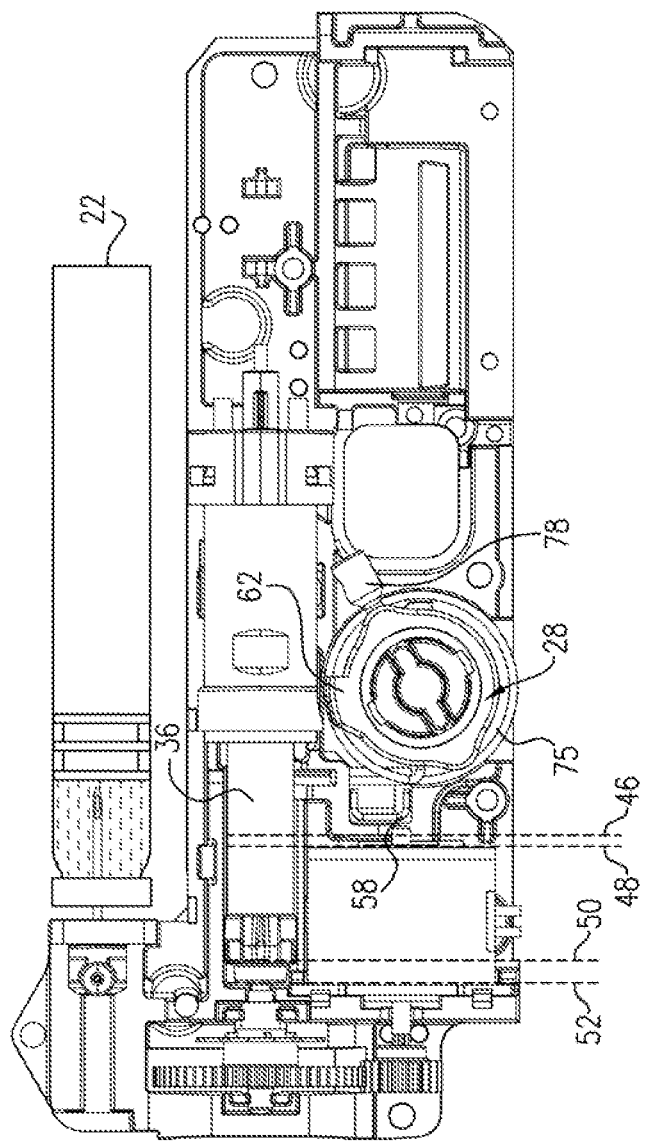
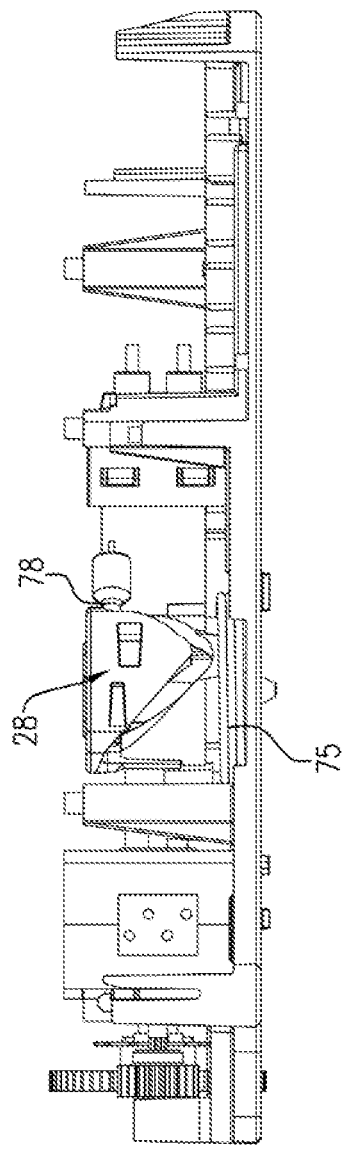
FIG. 5A
FIG. 5B

```
┌─────────────────────────────────────┐
│   DELIVER THERAPEUTIC SUBSTANCE FROM A   │
│   THERAPEUTIC SUBSTANCE RESERVOIR TO THE │──── 88
│   SUBJECT VIA A FLUID PATH OF THE THERAPEUTIC │
│       SUBSTANCE DELIVERY DEVICE          │
└─────────────────────────────────────┘
                  │
                  ▼
┌─────────────────────────────────────┐
│   DISCONNECT THE THERAPEUTIC SUBSTANCE   │
│   DELIVERY DEVICE FROM THE THERAPEUTIC   │──── 90
│        SUBSTANCE RESERVOIR           │
└─────────────────────────────────────┘
                  │
                  ▼
┌─────────────────────────────────────┐
│  APPLY SUCTION TO DRAW AIR INTO THE FLUID PATH │──── 92
└─────────────────────────────────────┘
                  │
                  ▼
┌─────────────────────────────────────┐
│   DRIVE THE AIR TOWARDS THE SUBJECT TO   │
│   DELIVER THERAPEUTIC SUBSTANCE WITHIN   │──── 94
│      THE FLUID PATH TO THE SUBJECT       │
└─────────────────────────────────────┘
```

FIG. 7

DRAWING DRUG FROM A VIAL

CROSS-REFERENCE TO RELATED APPLICATIONS

The present application is a Continuation of U.S. Ser. No. 16/591,848, filed Oct. 3, 2019, published as US 2020/0108201 to Ben-David, which claims the priority of:

(a) U.S. 62/741,572 to Ben-David, filed Oct. 5, 2018 entitled, "Triggering sequence," and (b) U.S. 62/805,021 to Yosef, filed Feb. 13, 2019, entitled, "Drawing drug from a vial."

Each of the above applications is incorporated herein by reference.

FIELD OF THE INVENTION

The present invention relates generally to delivery of a therapeutic substance to a subject, and more specifically to wearable drug delivery devices utilizing therapeutic substance reservoirs.

BACKGROUND

Pumps are often used in the medical industry for delivering therapeutic substances, e.g., drugs, to subjects. Therapeutic substances such as saline solution, insulin, antibiotics, and chemotherapy drugs may all be delivered to a subject with medical pumps. While hospitalization is required for delivery of some therapeutic substances, other therapeutic substances, such as for example insulin, do not require that the subject be in the hospital. Medical pumps enable patients to go about their daily lives while receiving a therapeutic substance.

SUMMARY OF THE INVENTION

Apparatus, such as for example a therapeutic substance delivery device, e.g., a wearable medical patch pump, is provided for use with a therapeutic substance reservoir. Within the therapeutic substance delivery device is a fluid path. The upstream end of the fluid path comprises a reservoir needle that penetrates the therapeutic substance reservoir. The downstream end of the fluid path comprises a body needle. A body needle injection mechanism typically advances the body needle into the body of a subject and retracts the body needle from the body of the subject. For some applications, an electromechanical pumping assembly, shaped to define a pump chamber and comprising a plunger disposed within the pump chamber, pumps the therapeutic substance from the therapeutic substance reservoir to the subject.

A plurality of operations combine to operate the therapeutic substance delivery device. The plurality of operations typically include driving the reservoir needle to penetrate the therapeutic substance reservoir, advancing the body needle into the body of the subject, withdrawing the therapeutic substance from the therapeutic substance reservoir, pumping the therapeutic substance into the subject, and retracting the body needle from the body of the subject (or a subset of these). The plunger of the electromechanical pumping assembly moves back and forth, e.g., linearly along a straight-line path, through a plurality of discrete motion phases. As the plunger moves back and forth, each of its motion phases activates a different one of the operations, such that at least some, and typically all, the operations of the therapeutic substance delivery device are actuated by the plunger's discrete back and forth motions. Thus, a first one of the motion phases actuates a first one of the abovementioned operations, and a second one of the motion phases operates a second one of the abovementioned operations.

A therapeutic substance reservoir is provided, e.g., a wearable medical patch pump, that engages with a therapeutic substance reservoir, such as for example, a non-collapsible drug vial that does not contain (or use) a movable plunger. A pump within the therapeutic substance reservoir draws the therapeutic substance from the reservoir into a pump chamber, e.g., a syringe, without changing the internal dimensions of the reservoir. Typically, air is allowed into the reservoir while the drug is being drawn so as to avoid vacuum building up within the reservoir. The therapeutic substance inside the pump chamber is then delivered to the subject.

In order to draw the therapeutic substance from the reservoir, a volume of the therapeutic substance within the reservoir is calculated and an orientation sensor, e.g., an accelerometer or gyroscope, is used to determine the orientation of the therapeutic substance delivery device with respect to gravity. For different volumes of therapeutic substance remaining in the reservoir, certain corresponding orientations of the therapeutic substance delivery device will allow for therapeutic substance to be drawn from the reservoir while other orientations of the therapeutic substance reservoir will not allow for therapeutic substance to be drawn from the reservoir. Thus, control circuitry within the therapeutic substance delivery device drives the pump to draw therapeutic substance from the reservoir in response to an indication that the combination of (i) the volume of the therapeutic substance within the reservoir and (ii) the orientation of the therapeutic substance delivery device with respect to gravity, allows for liquid to be drawn from the reservoir.

Typically, the therapeutic substance is drawn from the reservoir in response to the above described combination and substantially not in response to a set, i.e., predetermined, pumping schedule. Thus, the control circuitry may drive the therapeutic substance delivery device to draw therapeutic substance from the reservoir into the pump chamber, i.e., to refill the pump chamber, even if not all the therapeutic substance within the pump chamber has been delivered to the subject.

Thus, a patient is able to buy a standard commercially-available drug vial and insert it directly into the therapeutic substance delivery device, without having to use an intermediary filling apparatus to fill the therapeutic substance delivery device from the drug vial.

There is therefore provided, in accordance with some applications of the present invention, apparatus for delivering a therapeutic substance to a subject, the apparatus including:

a therapeutic substance delivery device configured to be engaged with a therapeutic substance reservoir, the therapeutic substance delivery device including:

a fluid path including a reservoir needle that is configured to penetrate the therapeutic substance reservoir;

a body needle;

a body needle injection mechanism configured to (a) advance the body needle into a body of the subject and (b) retract the body needle from the body of the subject; and an electromechanical pumping assembly (a) configured to pump the therapeutic substance from the therapeutic substance reservoir to the subject, (b) shaped to define a pump chamber, and (c) including a plunger disposed within the pump chamber, the plunger configured to move back and forth through a plurality of discrete motion phases, a first one of the motion phases of the plunger actuating a first operation selected from the group consisting of: driving the reservoir needle to penetrate the therapeutic substance reservoir, advancing the body needle into the body of the subject, withdrawing the therapeutic substance from the therapeutic substance reservoir, pumping the therapeutic substance into the subject, and retracting the body needle, and a second one of the motion phases of the plunger actuating a second operation selected from the group.

For some applications, the electromechanical pumping assembly is arranged such that the first one of the motion phases actuates a single operation selected from the group, and the second one of the motion phases actuates two operations selected from the group.

For some applications, the electromechanical pumping assembly is arranged such that the motion phase that actuates the operation of advancing the body needle into the body of the subject also actuates the operation of withdrawing the therapeutic substance from the therapeutic substance reservoir.

For some applications, the electromechanical pumping assembly is arranged such that:

(a) the first motion phase actuates the operation of driving the reservoir needle to penetrate the therapeutic substance reservoir, (b) the second motion phase actuates the operation of advancing the body needle into the body of the subject, and (c) the first motion phase is before the second motion phase.

For some applications, the first motion phase of the plunger is in a first direction, and wherein the second motion phase of the plunger is in a second direction.

For some applications:

a third one of the motion phases of the plunger actuates a third operation selected from the group, the third motion phase of the plunger is in the first direction, and the electromechanical pumping assembly is arranged such that (a) the first motion phase is before the second motion phase, and (b) the second motion phase is before the third motion phase.

For some applications:

a fourth one of the motion phases of the plunger actuates a fourth operation selected from the group, the fourth motion phase of the plunger is in the second direction, and the electromechanical pumping assembly is arranged such that the third motion phase is before the fourth motion phase.

For some applications:

the plunger is coupled to the reservoir needle, the first one of the motion phases is a maximal advance of the plunger in the first direction, the first selected operation is driving the reservoir needle to penetrate the therapeutic substance reservoir, and the plunger and the reservoir needle are arranged such that the maximal advance of the plunger drives the reservoir needle to penetrate the therapeutic substance reservoir.

For some applications, the electromechanical pumping assembly is arranged such that following the first motion phase that is the maximal advance of the plunger in the first direction, no other motion phase that is an advance of the plunger in the first direction is an advance of the plunger as large as the maximal advance.

For some applications:

the second motion phase is a partial retraction of the plunger in the second direction, the partial retraction being less than a maximal retraction of the plunger in the second direction, the second selected operation is advancing the body needle into the body of the subject, the plunger and the body needle injection mechanism being arranged such that the partial retraction of the plunger in the second direction causes the body needle injection mechanism to advance the body needle into the body of the subject, and the electromechanical pumping assembly is arranged such that the first motion phase is before the second motion phase.

For some applications:

the second motion phase is a partial retraction of the plunger in the second direction, the partial retraction being less than a maximal retraction of the plunger in the second direction, the second selected operation is advancing the body needle into the body of the subject, and the plunger and the body needle injection mechanism are arranged such that the partial retraction of the plunger in the second direction causes the body needle injection mechanism to advance the body needle into the body of the subject.

For some applications, the electromechanical pumping assembly is arranged such that the second motion phase actuates the operation of advancing the body needle into the body of the subject and the operation of withdrawing the therapeutic substance from the therapeutic substance reservoir.

For some applications:

a third one of the motion phases of the plunger actuates a third operation selected from the group, the third one of the motion phases of the plunger is a partial advance of the plunger in the first direction, the third selected operation is pumping the therapeutic substance into the subject, and the electromechanical pumping assembly is arranged such that the partial advance of the plunger causes therapeutic substance inside the pump chamber to be pumped to the subject.

For some applications:

a third one of the motion phases of the plunger actuates a third operation selected from the group, a fourth one of the motion phases of the plunger actuates a fourth operation selected from the group, the fourth motion phase is a maximal retraction of the plunger in the second direction, the fourth selected operation is retracting the body needle, and the plunger and the body needle injection mechanism are arranged such that maximal retraction of the plunger causes the body needle injection mechanism to retract the body needle.

For some applications, the electromechanical pumping assembly is arranged such that no other motion phase that is a retraction of the plunger in the second direction is a retraction of the plunger as large as the maximal retraction.

For some applications, the plunger and the reservoir needle are arranged such that the maximal retraction of the plunger retracts the reservoir needle from the therapeutic substance reservoir.

For some applications, the electromechanical pumping assembly is arranged such that the plurality of discrete motion phases sequentially actuate all of the operations in the group.

For some applications:

the body needle injection mechanism includes a barrel cam coupled to (i) the body needle and (ii) a pretensioned torsion spring, and the barrel cam is disposed within the therapeutic substance delivery device such that (a) as the pretensioned torsion spring is partially released the barrel cam rotates through a first rotational motion, the first rotational motion of the barrel cam advancing the body needle into the body of the subject, and (b) as the pretensioned torsion spring is further released the barrel cam rotates through a second rotational motion, the second rotational motion of the barrel cam retracting the body needle from the body of the subject.

For some applications, the first rotational motion of the barrel cam is a rotation of the barrel cam through 45-135 degrees.

For some applications, the second rotational motion of the barrel cam is a rotation of the barrel cam to 90-270 degrees from a starting position of the barrel cam.

For some applications, the therapeutic substance reservoir includes a cartridge having a movable stopper disposed within the cartridge and configured to move within the cartridge as therapeutic substance is drawn out of the cartridge.

For some applications, the internal dimensions of the reservoir do not change in response to the therapeutic substance being withdrawn from the reservoir by the pumping assembly.

For some applications, maximum internal dimensions of the pump chamber are smaller than the internal dimensions of the reservoir.

For some applications, the therapeutic substance reservoir is a prefilled reservoir.

For some applications, the therapeutic substance reservoir is configured to be filled by the subject prior to engagement of the therapeutic substance reservoir with the therapeutic substance delivery device.

For some applications, the electromechanical pumping assembly is arranged such that the first one of the motion phases actuates a single operation selected from the group, and the second one of the motion phases actuates two operations selected from the group.

For some applications, the electromechanical pumping assembly is arranged such that the motion phase that actuates the operation of advancing the body needle into the body of the subject also actuates the operation of withdrawing the therapeutic substance from the therapeutic substance reservoir.

For some applications, the electromechanical pumping assembly is arranged such that:

(a) the first motion phase actuates the operation of driving the reservoir needle to penetrate the therapeutic substance reservoir, (b) the second motion phase actuates the operation of advancing the body needle into the body of the subject, and (c) the first motion phase is before the second motion phase.

For some applications, the first motion phase of the plunger is in a first direction, and wherein the second motion phase of the plunger is in a second direction.

For some applications:

(a) the therapeutic substance delivery device further includes an air needle configured to penetrate the reservoir and to allow air from within the therapeutic substance delivery device to enter the reservoir, and (b) the operation of driving the reservoir needle to penetrate the therapeutic substance reservoir includes (i) driving the reservoir needle to penetrate the reservoir, and (ii) driving the air needle to penetrate the reservoir.

For some applications, the plunger is coupled to (a) the reservoir needle, and (b) the air needle, the first one of the motion phases is a maximal advance of the plunger in the first direction, the first selected operation is (i) driving the reservoir needle to penetrate the reservoir, and (ii) driving the air needle to penetrate the reservoir, and the plunger, the reservoir needle, and the air needle are arranged such that the maximal advance of the plunger drives (a) the reservoir needle, and (b) the air needle, to penetrate the therapeutic substance reservoir.

For some applications, the electromechanical pumping assembly is arranged such that following the first motion phase that is the maximal advance of the plunger in the first direction, no other motion phase that is an advance of the plunger in the first direction is an advance of the plunger as large as the maximal advance.

For some applications:

the second motion phase is a partial retraction of the plunger in the second direction, the partial retraction being less than a maximal retraction of the plunger in the second direction, the second selected operation is advancing the body needle into the body of the subject, wherein the plunger and the body needle injection mechanism are arranged such that the partial retraction of the plunger in the second direction causes the body needle injection mechanism to advance the body needle into the body of the subject, and the electromechanical pumping assembly is arranged such that the first motion phase is before the second motion phase.

For some applications, a third one of the motion phases of the plunger actuates a third operation selected from the group, the third motion phase of the plunger is in the first direction, and the electromechanical pumping assembly is arranged such that (a) the first motion phase is before the second motion phase, and (b) the second motion phase is before the third motion phase.

For some applications, a fourth one of the motion phases of the plunger actuates a fourth operation selected from the group, the fourth motion phase of the plunger is in the second direction, and the electromechanical pumping assembly is arranged such that the third motion phase is before the fourth motion phase.

For some applications, the second motion phase is a partial retraction of the plunger in the second direction, the partial retraction being less than a maximal retraction of the plunger in the second direction, the second selected operation is advancing the body needle into the body of the subject, and the plunger and the body needle injection mechanism are arranged such that the partial retraction of the plunger in the second direction causes the body needle injection mechanism to advance the body needle into the body of the subject.

For some applications, the electromechanical pumping assembly is arranged such that the second motion phase actuates the operation of advancing the body needle into the body of the subject and the operation of withdrawing the therapeutic substance from the therapeutic substance reservoir.

For some applications, a third one of the motion phases of the plunger actuates a third operation selected from the group, the third one of the motion phases of the plunger is a partial advance of the plunger in the first direction, the third selected operation is pumping the therapeutic substance into the subject, and the electromechanical pumping assembly is arranged such that the partial advance of the plunger causes therapeutic substance inside the pump chamber to be pumped to the subject.

For some applications, the apparatus further includes:

an orientation sensor coupled to the therapeutic substance delivery device and configured to generate an output indicative of an orientation of the therapeutic substance delivery device with respect to gravity; and control circuitry configured to drive the electromechanical pumping assembly to:
  (a) calculate a volume of the therapeutic substance disposed within the reservoir,
  (b) in response to (i) the calculated volume of the therapeutic substance disposed within the reservoir, in combination with (ii) an output from the orientation sensor that the therapeutic substance delivery device is in an orientation that allows the therapeutic substance to be drawn from the reservoir, drive the pumping assembly to perform the second motion phase of the plunger, wherein the selected second operation is withdrawing the therapeutic substance into the pump chamber, and
  (c) drive the pumping assembly to perform the third motion phase of the plunger to pump.

For some applications, the control circuitry is configured such that the second motion phase of the plunger is performed substantially not in response to a predetermined therapeutic substance delivery schedule.

For some applications, the control circuitry is configured to drive the pumping assembly to interrupt the third motion phase of the plunger by repeating the second motion phase of the plunger.

For some applications, the control circuitry is configured to drive the pumping assembly to perform the second motion phase of the plunger regardless of whether there is therapeutic substance within the pump chamber.

For some applications:

a third one of the motion phases of the plunger actuates a third operation selected from the group, a fourth one of the motion phases of the plunger actuates a fourth operation selected from the group, the fourth motion phase is a maximal retraction of the plunger in the second direction, the fourth selected operation is retracting the body needle, and the plunger and the body needle injection mechanism are arranged such that maximal retraction of the plunger causes the body needle injection mechanism to retract the body needle.

For some applications, the electromechanical pumping assembly is arranged such that no other motion phase that is a retraction of the plunger in the second direction is a retraction of the plunger as large as the maximal retraction.

For some applications, the plunger and the reservoir needle are arranged such that the maximal retraction of the plunger retracts the reservoir needle from the therapeutic substance reservoir.

For some applications, the electromechanical pumping assembly is arranged such that the plurality of discrete motion phases sequentially actuate all of the operations in the group.

For some applications, the body needle injection mechanism includes a barrel cam coupled to (i) the body needle and (ii) a pretensioned torsion spring, and the barrel cam is disposed within the therapeutic substance delivery device such that (a) as the pretensioned torsion spring is partially released the barrel cam rotates through a first rotational motion, the first rotational motion of the barrel cam advancing the body needle into the body of the subject, and (b) as the pretensioned torsion spring is further released the barrel cam rotates through a second rotational motion, the second rotational motion of the barrel cam retracting the body needle from the body of the subject.

For some applications, the first rotational motion of the barrel cam is a rotation of the barrel cam through 45-135 degrees.

For some applications, the second rotational motion of the barrel cam is a rotation of the barrel cam to 90-270 degrees from a starting position of the barrel cam.

For some applications, the apparatus further includes:

an orientation sensor coupled to the therapeutic substance delivery device and configured to generate an output indicative of an orientation of the therapeutic substance delivery device with respect to gravity; and control circuitry configured to drive the electromechanical pumping assembly to:
  (a) calculate a volume of the therapeutic substance disposed within the reservoir,
  (b) in response to (i) the calculated volume of the therapeutic substance disposed within the reservoir, in combination with (ii) an output from the orientation sensor that the therapeutic substance delivery device is in an orientation that allows the therapeutic substance to be drawn from the reservoir, drive the pumping assembly to perform the first motion phase of the plunger, wherein the selected first operation is withdrawing the therapeutic substance into the pump chamber, and
  (c) drive the pumping assembly to perform the second motion phase of the plunger to pump, wherein the selected second operation is pumping the therapeutic substance from the pump chamber to the subject.

For some applications, the control circuitry is configured such that the first motion phase of the plunger is performed substantially not in response to a predetermined therapeutic substance delivery schedule.

For some applications, the control circuitry is configured to drive the pumping assembly to interrupt the second motion phase of the plunger by repeating the first motion phase of the plunger.

For some applications, the control circuitry is configured to drive the pumping assembly to perform the first motion phase of the plunger regardless of whether there is therapeutic substance within the pump chamber.

There is further provided, in accordance with some applications of the present invention, apparatus for delivering a therapeutic substance to a subject, the apparatus including:

a therapeutic substance delivery device configured to be engaged with a therapeutic substance reservoir, the therapeutic substance delivery device including:
  a fluid path configured to engage with the therapeutic substance reservoir;
  a body needle;

a body needle injection mechanism configured to advance the body needle into a body of the subject; and a pumping assembly (a) configured to pump the therapeutic substance from the therapeutic substance reservoir to the subject, (b) shaped to define a pump chamber, and (c) including a plunger disposed within the pump chamber, the plunger configured to move back and forth through a plurality of discrete motion phases, a first one of the motion phases of the plunger actuating a first operation selected from the group consisting of: engaging the fluid path with the therapeutic substance reservoir, advancing the body needle into the body of the subject, withdrawing the therapeutic substance from the therapeutic substance reservoir, pumping the therapeutic substance into the subject, and retracting the body needle from the body of the subject, and a second one of the motion phases of the plunger actuating a second operation selected from the group.

For some applications, the pumping assembly is an electromechanical pumping assembly.

For some applications, the fluid path includes a needle that is configured to penetrate the therapeutic substance reservoir.

For some applications, the operation of engaging the fluid path with the therapeutic substance reservoir includes driving the reservoir needle to penetrate the therapeutic substance reservoir.

For some applications, the body needle injection mechanism is configured to retract the body needle from the body of the subject.

For some applications, the therapeutic substance reservoir includes a cartridge having a movable stopper disposed within the cartridge and configured to move within the cartridge as therapeutic substance is drawn out of the cartridge.

For some applications, the therapeutic substance reservoir includes a therapeutic substance reservoir wherein the internal dimensions of the reservoir do not change in response to the therapeutic substance being withdrawn from the reservoir by the pumping assembly.

For some applications, (a) the therapeutic substance delivery device further includes an air needle configured to penetrate the reservoir and to allow air from within the therapeutic substance delivery device to enter the reservoir, and (b) the operation of driving the reservoir needle to penetrate the therapeutic substance reservoir includes (i) driving the reservoir needle to penetrate the reservoir, and (ii) driving the air needle to penetrate the reservoir.

There is further provided, in accordance with some applications of the present invention, a method for delivering a therapeutic substance to a subject, the method including:

delivering the therapeutic substance from a therapeutic substance reservoir to the subject via a fluid path of the therapeutic substance delivery device;

disconnecting the therapeutic substance delivery device from the therapeutic substance reservoir;

subsequently, applying suction to draw air into the fluid path; and driving the air towards the subject to deliver therapeutic substance within the fluid path to the subject.

There is further provided, in accordance with some applications of the present invention, a method for delivering a therapeutic substance to a subject, the method including:

delivering the therapeutic substance from a therapeutic substance reservoir to the subject via a fluid path of the therapeutic substance delivery device;

subsequently, applying suction to draw air into the fluid path;

detecting an amount of air within the fluid path; and terminating the applying of the suction in response to the detected amount of air within the fluid path reaching an end-of-treatment air threshold.

There is further provided, in accordance with some applications of the present invention, apparatus for delivering a therapeutic substance to a subject, the apparatus including:

a therapeutic substance delivery device:

(a) configured to engage with a therapeutic substance reservoir, and (b) including a pump configured to draw the therapeutic substance from the reservoir into a pump chamber disposed within the therapeutic substance delivery device without changing the internal dimensions of the reservoir, the volume of the therapeutic substance within the pump chamber varying in response to changes in the internal dimensions of the pump chamber;

an orientation sensor coupled to the therapeutic substance delivery device and configured to generate an output indicative of an orientation of the therapeutic substance delivery device with respect to gravity; and control circuitry configured to drive the pump to:

(a) calculate a volume of the therapeutic substance disposed within the reservoir, (b) drive the pump to draw the therapeutic substance into the pump chamber in response to (i) the calculated volume of the therapeutic substance disposed within the reservoir, in combination with (ii) an output from the orientation sensor that the therapeutic substance delivery device is in an orientation that allows the therapeutic substance to be drawn from the reservoir, and (c) drive the pump to deliver the therapeutic substance from the pump chamber to the subject.

For some applications, maximum internal dimensions of the pump chamber are smaller than the internal dimensions of the reservoir.

For some applications, the therapeutic substance reservoir is a prefilled reservoir.

For some applications, the therapeutic substance reservoir is configured to be filled by the subject prior to engagement of the therapeutic substance reservoir with the therapeutic substance delivery device.

For some applications, the orientation sensor includes an accelerometer.

There is further provided, in accordance with some applications of the present invention, a method for delivering a therapeutic substance to a subject, the method including:

using a therapeutic substance delivery device:

drawing the therapeutic substance from a therapeutic substance reservoir into a pump chamber of the therapeutic delivery device, and delivering the therapeutic substance from the pump chamber to the subject, the drawing of the therapeutic substance being:

(i) without changing the internal dimensions of the reservoir, and (ii) substantially in response to (a) a volume of therapeutic substance in the reservoir, in combination with (b) an orientation of the therapeutic substance delivery device.

For some applications, the drawing of the therapeutic substance is substantially not in response to a predetermined therapeutic substance delivery schedule.

For some applications, drawing the therapeutic substance from the therapeutic substance reservoir includes interrupting the delivering of the therapeutic substance from the pump chamber by filling the pump chamber with therapeutic substance from the therapeutic substance reservoir.

For some applications, drawing the therapeutic substance from the reservoir includes drawing the therapeutic substance from the reservoir regardless of whether there is therapeutic substance within the pump chamber.

The present invention will be more fully understood from the following detailed description of applications thereof, taken together with the drawings, in which:

BRIEF DESCRIPTION OF THE DRAWINGS

FIGS. 2A-C are schematic illustrations of different perspectives of the therapeutic substance delivery device of FIGS. 1A-C and a reservoir needle after a first motion phase of a plunger, in accordance with some applications of the present invention;

FIGS. 3A-B are schematic illustrations of different perspectives of the therapeutic substance delivery device showing a second motion phase of the plunger and a body needle injection mechanism rotating to drive the body needle into the body of a subject, in accordance with some applications of the present invention;

FIGS. 4A-B are schematic illustrations of different perspectives of the therapeutic substance delivery device showing a third motion phase of the plunger, in accordance with some applications of the present invention;

FIGS. 5A-B are schematic illustrations of different perspectives of the therapeutic substance delivery device showing a fourth motion phase of the plunger, in accordance with some applications of the present invention;

FIG. 7 is a flowchart showing a method of delivering a therapeutic substance to a subject, in accordance with some applications of the present invention;

DETAILED DESCRIPTION

Figure 1A:
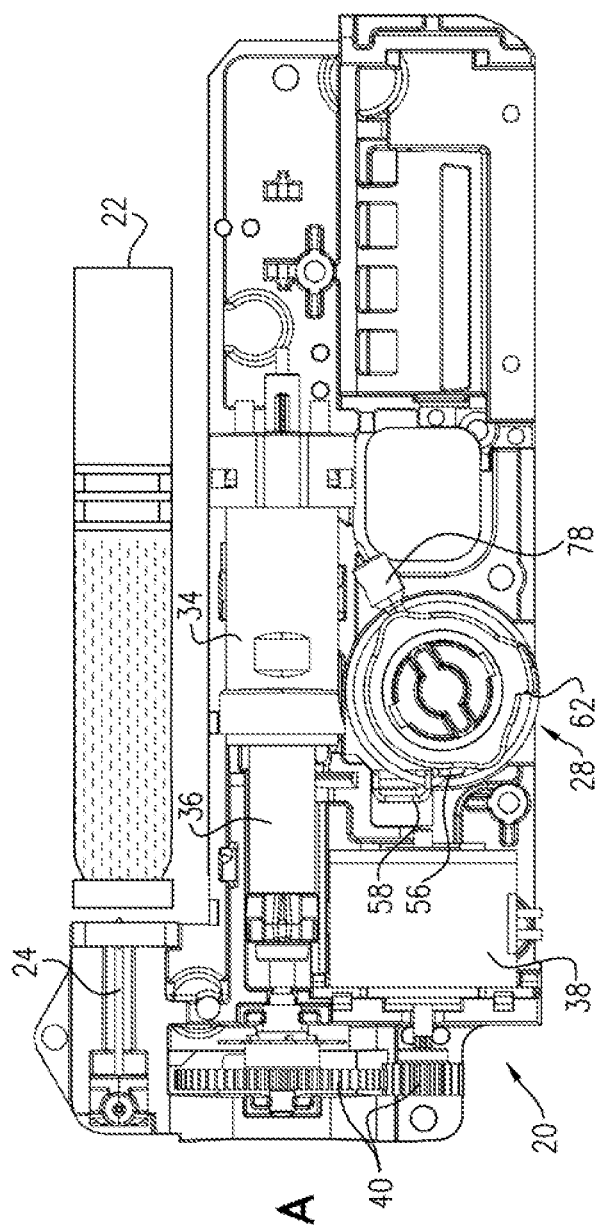
FIGS. 1A-C are schematic illustrations of different perspectives of a therapeutic substance delivery device showing a plurality of internal mechanisms at their respective start positions, in accordance with some applications of the present invention.
Figure 1B:
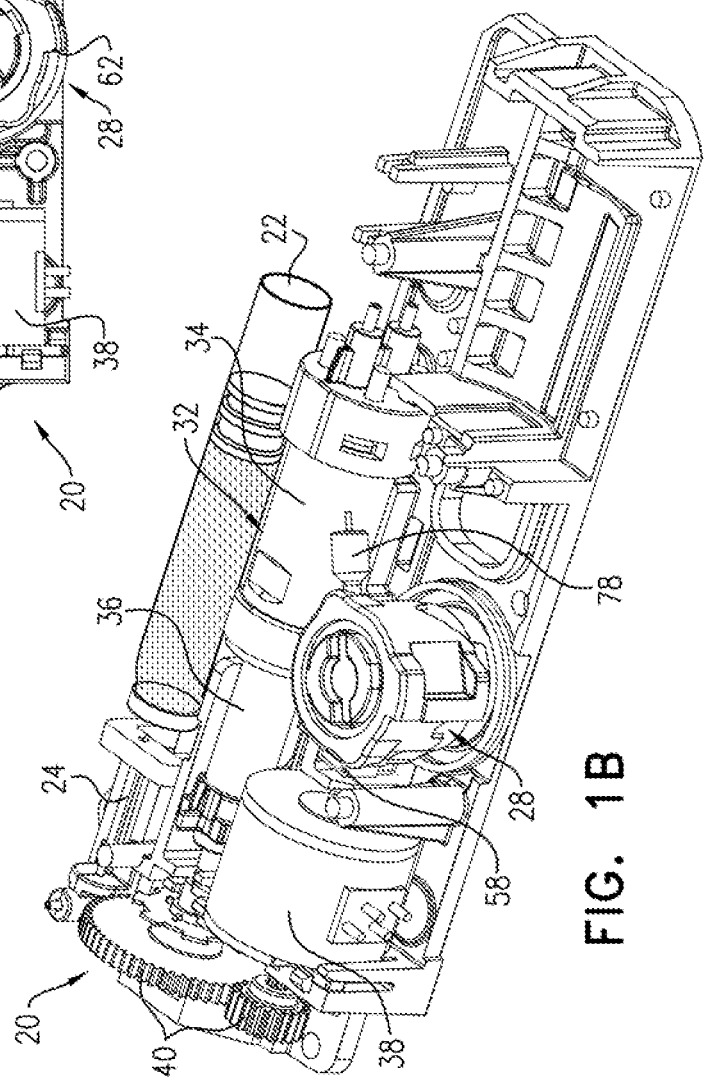
Figure 1C:
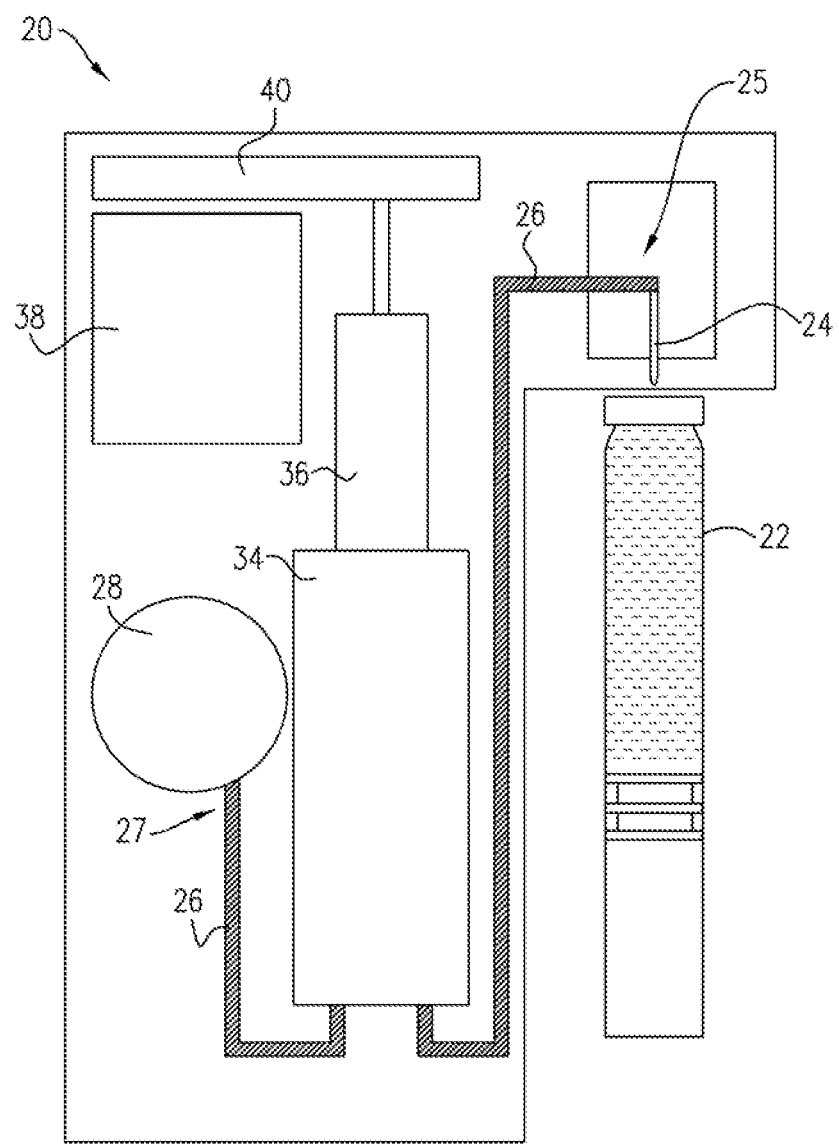

Reference is now made to FIGS. 1A-C, which are schematic illustrations of different perspectives of a therapeutic substance delivery device 20 showing a plurality of internal mechanisms at their respective start positions, in accordance with some applications of the present invention. Typically, therapeutic substance delivery device 20 engages with a therapeutic substance reservoir 22. Therapeutic substance reservoir 22 may be prefilled, or alternatively, may be fillable by the user. Therapeutic substance reservoir 22 may be replaceable. For some applications, therapeutic substance reservoir 22 is a cartridge with a movable stopper that is disposed within the cartridge and moves within the cartridge as the therapeutic substance is drawn out of the cartridge.

Figure 6:
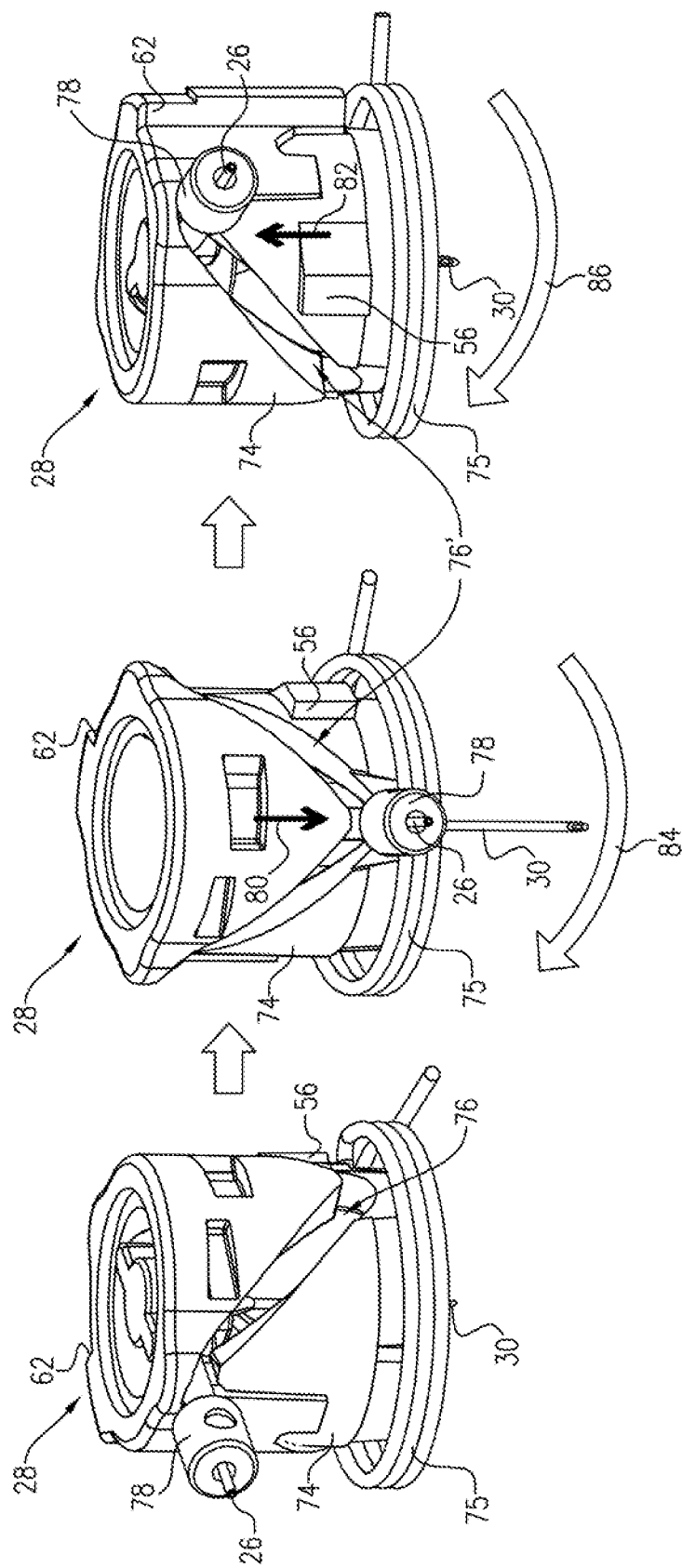
FIG. 6 is a schematic illustration of the body needle injection mechanism, in accordance with some applications of the present invention.

For some applications, a fluid path 26 (shown in FIG. 1C) within therapeutic substance delivery device 20 comprises a reservoir needle 24 at an upstream end 25. Reservoir needle 24 is positioned to penetrate therapeutic substance reservoir 22 (such as is further described hereinbelow with reference to FIGS. 2A-C). Alternatively, fluid path 26 may engage with therapeutic substance reservoir 22 via a connector that is not a needle. A body needle injection mechanism 28 which is coaxial with a body needle 30 (such as is shown in FIG. 6) is disposed at a downstream end 27 of fluid path 26. As further described hereinbelow with reference to FIGS. 3A-B and FIGS. 5A-B, body needle injection mechanism 28 typically advances body needle 30 into the body of the subject and retracts body needle 30 from the body of the subject. For some applications, body needle injection mechanism 28 may only advance body needle 30 into the body of the subject.

For some applications, an electromechanical pumping assembly 32 (FIG. 1B) pumps the therapeutic substance from therapeutic substance reservoir 22 to the subject via fluid path 26. Electromechanical pumping assembly 32 is shaped to define a pump chamber 34 and comprises a plunger 36 disposed within pump chamber 34. Plunger 36 moves back and forth through a plurality of discrete motion phases as further described hereinbelow. Typically, a motor 38 drives the motion of plunger 36 via a series of gears 40, one of which is coupled to a screw that is coaxial with plunger 36 so as to translate rotational motion of gears 40 into linear motion of plunger 36.

For some applications, the pumping assembly may not be electromechanical, i.e., pumping assembly 32 may be driven to pump the therapeutic substance from therapeutic substance reservoir 22 to the subject via a driving mechanism that is not electromechanical, e.g., a pneumatic driving mechanism, or a mechanical driving mechanism such as a spring-driven mechanism.

As plunger 36 moves back and forth through the plurality of discrete motion phases, each motion phase of the plunger activates an operation of therapeutic substance delivery device 20. Thus, a first one of the motion phases actuates a first one of the operations, and a second one of the motion phases operates a second one of the operations. As described hereinabove, the operations typically include driving reservoir needle 24 to penetrate therapeutic substance reservoir 22, advancing body needle 30 into the body of the subject, withdrawing the therapeutic substance from therapeutic substance reservoir 22, pumping the therapeutic substance into the subject, and retracting body needle 30 from the body of the subject (or a subset of these). Optionally, the plurality of operations may further include retracting reservoir needle 24 from therapeutic substance reservoir 22.

For some applications, the operations are activated in a sequence as will be described hereinbelow with reference to motion phases 1-4 of the plunger's motion. The sequence of operations, however, is not limiting and the operations may be activated by the plunger's motion in any sequence. For some applications, only some, e.g., two or three, of the operations may be activated by the motion of the plunger.

Reference is now made to FIGS. 2A-C, which are schematic illustrations of different perspectives of therapeutic substance delivery device 20 and of reservoir needle 24 after a first motion phase of plunger 36, in accordance with some applications of the present invention. Typically, the first motion of plunger 36 is a maximal advance of plunger 36 in a first direction to drive reservoir needle 24 to penetrate therapeutic substance reservoir 22. For some applications, reservoir needle 24 is mounted to a needle slider 42. A rigid connecting element 44, e.g., a rigid bracket (FIG. 2C), connected to needle slider 42 is positioned such that plunger 36 pushes on rigid connecting element 44 as plunger 36 moves to the maximal advance in the first direction. Thus, rigid connecting element 44 drives reservoir needle 24 to penetrate therapeutic substance reservoir 22 as plunger 36 moves to the maximal advance in the first direction. For some applications, reservoir needle 24 is only driven in the first direction to penetrate therapeutic substance reservoir 22, e.g., after being pushed in the first direction by plunger 36, rigid connecting element 44 is not connected to plunger 36 and does not retract along with a retraction of plunger 36. Alternatively, after the therapeutic substance has been pumped from therapeutic substance reservoir 22 to the subject, rigid connecting element 44 may be reconnected to plunger 36 so as to drive needle slider 42 in a second direction opposite the first direction as plunger 36 retracts in order to retract reservoir needle 24 from therapeutic substance reservoir 22.

FIG. 2A shows a top-view of (a) plunger 36 after performing the maximal advance in the first direction that drives reservoir needle 24 to penetrate therapeutic substance reservoir 22, and (b) reservoir needle 24 after having penetrated therapeutic substance reservoir 22. As further described hereinbelow, electromechanical pumping assembly 32 is arranged such that, while other motion phases of plunger 36 may include advances of plunger 36 in the first direction, typically no other motion phase that is an advance of the plunger in the first direction is an advance of the plunger as large as the maximal advance. Dashed line 46 shows the maximal advance of plunger 36. Dashed line 48 shows a point at which the plunger may advance to during a different motion phase that is a partial advance of plunger 36, such as described hereinbelow with reference to FIGS. 4A-B.

Reference is now made to FIGS. 3A-B, which are schematic illustrations of different perspectives of therapeutic substance delivery device 20 showing a second motion phase of plunger 36 and body needle injection mechanism 28 rotating to drive body needle 30 into the body of the subject, in accordance with some applications of the present invention. Typically, the second phase of plunger 36 is in a second direction, e.g., the first motion phase is a maximal advance of plunger 36 as described hereinabove, and the second motion phase is a retraction of plunger 36. For some applications, the second motion phase of plunger 36 is a partial retraction of plunger 36 which causes body needle injection mechanism 28 to advance body needle 30 into the body of the subject. Typically, the partial retraction of plunger 36 is less than a maximal retraction of plunger 36 in the second direction. Dashed line 50 indicates a stopping point of plunger 36 after the partial retraction. Dashed line 52 indicates a stopping point of plunger 36 for a maximal retraction of plunger 36.

For some applications, body needle injection mechanism 28 operates based on rotation caused by a preloaded torsion spring 75 (shown more fully in FIG. 6). In its start position, such as is shown in FIG. 1, a first protrusion 56 of body needle injection mechanism 28 is engaged with a stop 58, e.g., a rigid bracket, that prevents body needle injection mechanism 28 from rotating. Stop 58 is typically positioned such that it is pushed by plunger 36 during retraction of plunger 36 in the second direction. The second motion phase of plunger 36, i.e., the partial retraction of plunger 36 pushes stop 58, causing stop 58 to shift a first amount, which in turn disengages stop 58 from first protrusion 56. Thus, body needle injection mechanism 28 is allowed to move through a first rotation due to the preloaded torsion spring. The progression from FIG. 2A to FIG. 3A shows body needle injection mechanism 28 rotating clockwise. A second protrusion 62 of body needle injection mechanism 28 engages with stop 58 so as to stop the first rotation of body needle injection mechanism 28 after body needle injection mechanism 28 has completed a rotation that is at least 45 degrees and/or less than 135 degrees, e.g., 90 degrees. As shown in FIG. 3B, as body needle injection mechanism 28 moves through the first rotation, body needle 30 is advanced into the body of the subject. Body needle 30 typically advances into the body of the subject perpendicular to the skin of the subject.

For some applications, whereas the first motion phase of plunger 36 activates a single operation, i.e., advancing reservoir needle 24 to penetrate therapeutic substance reservoir 22, the second motion phase of plunger 36 may activate two of the operations. For example, electromechanical pumping assembly 32 may be arranged such that as plunger 36 partially retracts during the second motion phase, the operation of withdrawing the therapeutic substance from therapeutic substance reservoir 22 is activated as well the operation of advancing body needle 30 into the body of the subject. Since reservoir needle 24 penetrated therapeutic substance reservoir 22 during the first motion phase, a fluid connection is established between pump chamber 34 and therapeutic substance reservoir 22. Therefore, it follows that as plunger 36 retracts from within pump chamber 34 during the second motion phase, therapeutic substance is drawn into pump chamber 34 via reservoir needle 24 and fluid path 26.

Reference is now made to FIGS. 4A-B, which are schematic illustrations of different perspectives of therapeutic substance delivery device 20 showing a third motion phase of plunger 36, in accordance with some applications of the present invention. Typically, the third motion phase of plunger 36 is a motion of plunger 36 in the first direction that actuates a third operation. For some applications, the third motion phase of plunger 36 is a partial advance of plunger 36 in the first direction in order to pump therapeutic substance within pump chamber 34 to the subject via fluid path 26 and body needle 30. Dashed line 48 illustrates a stopping point of plunger 36 after plunger 36 has partially advanced in the first direction during the third motion phase.

Typically, the first motion phase of plunger 36 is before the second motion phase and the second motion phase of plunger 36 is before the third motion phase. Thus, sequentially, reservoir needle 24 penetrates therapeutic substance reservoir 22 to initiate a fluid connection, body needle 30 is advanced into the body of the subject while therapeutic substance is withdrawn from therapeutic substance reservoir 22 into pump chamber 34, and subsequently the therapeutic substance is pumped from pump chamber 34 to the subject. The second (FIG. 3A) and third (FIG. 4A) motion phases may then be repeated in a reciprocating manner so as to repeatedly withdraw therapeutic substance from therapeutic substance reservoir 22 and into pump chamber 34 and pump it from pump chamber 34 to the subject.

As illustrated by FIGS. 3A and 4A, the repeated reciprocating motion of the second and third motion phases, pumps the therapeutic substance from therapeutic substance reservoir 22 to the subject while body needle 30 remains within the body of the subject. Since stop 58 is pushed by plunger 36 when plunger 36 retracts in the second direction, the partial advance of plunger 36 to pump the therapeutic substance from pump chamber 34 to the subject typically does not affect the position of stop 58. As the partial retraction of the second motion phase is repeated, plunger 36 typically returns to the same partial retraction position and thus stop 58 remains in place causing body needle 30 to remain within the body of the subject.

For some applications, two valves are disposed within therapeutic substance delivery device 20 such that (a) when the therapeutic substance is withdrawn from therapeutic substance reservoir 22 into pump chamber 34 a first valve is open, allowing the therapeutic substance to enter pump chamber 34, and a second valve is closed, preventing the therapeutic substance from leaving pump chamber 34, and (b) when therapeutic substance is being pumped from pump chamber 34 to the subject the first valve is closed, preventing more therapeutic substance from entering pump chamber 34, and the second valve is open, allowing the therapeutic substance to leave pump chamber 34 to the subject.

As illustrated by dashed lines 50 and 48, respectively, the retraction of plunger 36 to withdraw the therapeutic substance from therapeutic substance reservoir 22 and the advance of plunger 36 to pump the therapeutic substance to the subject are, respectively, a partial retraction and a partial advance. For some applications, electromechanical pumping assembly 32 is arranged such that no other motion phase that is an advance of plunger 36 in the first direction is an advance of the plunger as large as the maximal advance, e.g., the maximal advance that drives reservoir needle 24 to penetrate therapeutic substance reservoir 22, and no other motion phase that is a retraction of the plunger in the second direction, is a retraction of the plunger as large as the maximal retraction (further described hereinbelow). Avoiding a maximal advance and a maximal retraction of plunger 36 during the reciprocating motion of repeatedly withdrawing the therapeutic substance from the reservoir and pumping it to the subject allows plunger 36 to repeatedly retract and advance without causing activation of other operations which may occur when plunger 36 performs a maximal advance or a maximal retraction.

Reference is now made to FIGS. 5A-B, which are schematic illustrations of different perspectives of therapeutic substance delivery device 20 showing a fourth motion phase of plunger 36, in accordance with some applications of the present invention. Typically, the fourth motion phase of plunger 36 is in the second direction, i.e., a retraction of plunger 36, and actuates a fourth one of the operations. For some applications, the fourth motion phase of plunger 36 is a maximal retraction of plunger 36 in the second direction, which causes body needle injection mechanism 28 to retract body needle 30 from the body of the subject. As described hereinabove, for some applications, no other motion phase that is a retraction of plunger 36 is as large as the maximal retraction, so as to avoid triggering the retraction of the body needle 30 before therapeutic substance has finished being delivered to the subject. Dashed line 52 shows the stopping point for plunger 36 after plunger 36 performs the maximal retraction.

As described above with reference to FIG. 3, after the first rotation of body needle injection mechanism 28, second protrusion 62 is engaged with stop 58. The fourth motion phase of plunger 36, i.e., the maximal retraction of plunger 36, causes stop 58 to further shift a second amount, which in turn disengages stop 58 from second protrusion 62. Thus, body needle injection mechanism 28 is allowed to move through a second rotation of at least 90 degrees and/or less than 270 degrees from its original starting position (e.g., 180 degrees from its original starting position) due to preloaded torsion spring 75. For example, the second rotation may be a second 90-degree rotation following the first 90-degree rotation in the same direction.

For some applications, such as for example, when therapeutic substance reservoir 22 is replaceable, plunger 36 and reservoir needle 24 may be arranged such that the maximal retraction of plunger 36 retracts reservoir needle 24 from therapeutic substance reservoir 22. For example, the maximal retraction of plunger 36 may cause rigid connecting element 44 to reconnect to plunger 36 and retract needle slider 42 as plunger 36 moves to a maximal retraction, which in turn retracts reservoir needle 24.

While the order of the operations is not limiting, for some applications, plunger 36 moves through the discrete motion phases so as to sequentially activate all the operations. Thus, for example, the order of operations may be as follows:

- reservoir needle 24 is first driven to penetrate therapeutic substance reservoir 22,
- body needle injection mechanism 28 is then triggered to advance body needle 30 into the body of the subject while therapeutic substance is withdrawn from therapeutic substance reservoir 22 into pump chamber 34,
- the therapeutic substance is then pumped from pump chamber 34 to the subject (typically the phases of withdrawing the therapeutic substance from the reservoir and pumping it to the subject are repeated in a reciprocating manner), and
- body needle injection mechanism 28 is then triggered to retract body needle 30 from the body of the subject and, optionally, reservoir needle 24 is retracted from therapeutic substance reservoir 22. For some applications, both of these retractions are performed generally simultaneously.

Thus, in accordance with some applications of the present invention, the entire therapeutic substance delivery device 20 is operated by motor 38 driving plunger 36 to move back and forth through the plurality of motion phases, increasing simplicity of operation and saving space within therapeutic substance delivery device 20.

Reference is now made to FIG. 6, which is a schematic illustration of body needle injection mechanism 28, in accordance with some applications of the present invention. For some applications, body needle injection mechanism 28 is in the form of a barrel cam 74. Disposed around barrel cam 74 is a preloaded torsion spring 75. Barrel cam 74 is shaped to define angled slots 76 and 76'. Fluid path 26 is coupled to body needle 30 such that body needle 30 is coaxial with and disposed within barrel cam 74 and a rigid coupling segment 78 (shown also in FIGS. 1A-B, 2A-B, 3A-B, 4A-B, and 5A-B) is disposed (a) between body needle 30 and fluid path 26, and (b) within slot 76 of barrel cam 74. As barrel cam 74 is allowed to move through the first rotation (indicated by arrow 84) of at least 45 degrees and/or less than 135 degrees, e.g., 90 degrees, as described hereinabove with reference to FIG. 3A, angled slot 76 causes coupling segment 78 to move downwards with respect to therapeutic substance delivery device 20 (as indicated by downwards arrow 80), which in turn causes body needle 30 to advance towards the body of the subject. As barrel cam 74 is further allowed to rotate through the second rotation (typically in the same direction as the first rotation as indicated by arrow 86) of at least 90 degrees and/or less than 270 degrees from its original starting position, e.g., 180 degrees from start position, angled slot 76' causes coupling segment 78 to move upwards with respect to therapeutic substance delivery device 20 (as indicated by upwards arrow 82), which in turn causes body needle 30 to retract from the body of the subject.

The left image, center image, and right image of FIG. 6 are shown from different perspectives with respect to therapeutic substance delivery device 20. As barrel cam 74 rotates clockwise, coupling segment 78 moves directly down and up with respect to therapeutic substance delivery device 20. (By contrast barrel cam 74 does move rotationally with respect to therapeutic substance delivery device 20.) Coupling segment 78 typically does not move rotationally with respect to therapeutic substance delivery device 20.

In the transition from FIG. 2A (top view), to FIG. 3A (top view), coupling segment 78 does not rotate with respect to therapeutic substance delivery device 20, however as shown in the transition from FIG. 2B (perspective view) to FIG. 3B (side view), coupling segment 78 shifts downwards with respect to therapeutic substance delivery device 20 (corresponding to the transition between the left image and the center image in FIG. 6 as barrel cam 74 rotates). Thus, the left image of FIG. 6 corresponds to the position of coupling segment 78 in FIGS. 1A-B and FIGS. 2A-B, and the center image of FIG. 6 corresponds to the position of coupling segment 78 in FIGS. 3A-B and FIGS. 4A-B.

Similarly, in the transition from FIG. 4A (top view), to FIG. 5A (top view), coupling segment 78 does not rotate with respect to therapeutic substance delivery device 20, however as shown in the transition from FIG. 4B (side view) to FIG. 5B (side view), coupling segment 78 shifts upwards with respect to therapeutic substance delivery device 20 (corresponding to the transition between the center image and the right image in FIG. 6 as barrel cam 74 rotates again). Thus, the right image of FIG. 6 corresponds to the position of coupling segment 78 in FIGS. 5A-B.

Reference is now made to FIG. 7, which is a flowchart showing a method of delivering a therapeutic substance to a subject, in accordance with some applications of the present invention. After delivering therapeutic substance from a therapeutic substance reservoir to a subject via a fluid path of a therapeutic substance delivery device (step 88), the therapeutic substance delivery device may be disconnected from the therapeutic substance reservoir (step 90) and air drawn into the fluid path, e.g., by applying suction, (step 92) and driven to the subject (step 94) in order to deliver therapeutic substance remaining within the fluid path to the subject.

For some applications, this method may be performed using therapeutic substance delivery device 20 as described hereinabove with reference to FIGS. 1A-C, 2A-C, 3A-B, 4A-B, 5A-B, and 6, as well as with therapeutic substance delivery device 120 as described with reference to FIGS. 8-12, 14A-B, 15A-B, 16A-B, 17A-B, and 18A-B (further described hereinbelow). After therapeutic substance reservoir 22 has been depleted of therapeutic substance, some residual air within therapeutic substance reservoir 22 may be pumped through fluid path 26 by a repetition of the second and third motion phases as described hereinabove. By pumping this residual air to the subject, residual therapeutic substance within fluid path 26 is also pumped to the subject, thereby reducing dead volume.

Figure 12:
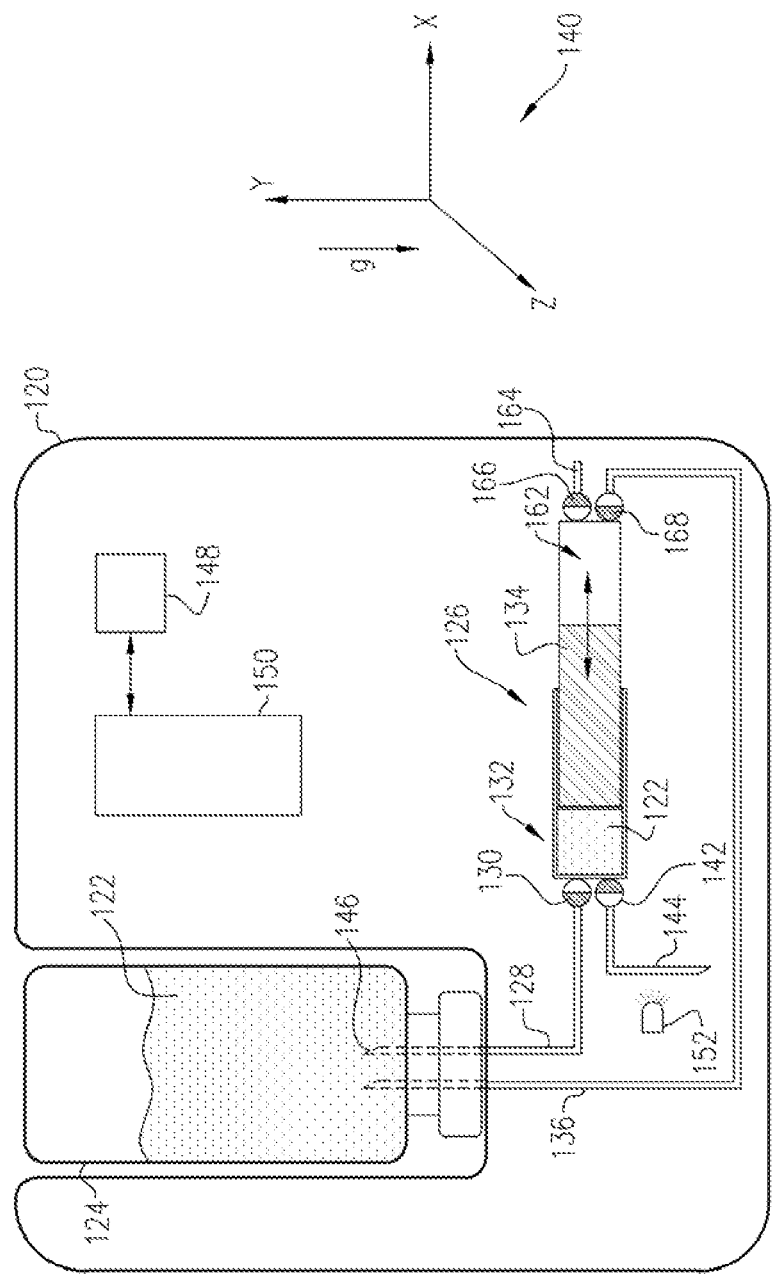
FIG. 12 is a schematic illustration of a therapeutic substance delivery device in accordance with some applications of the present invention.
Figure 13:
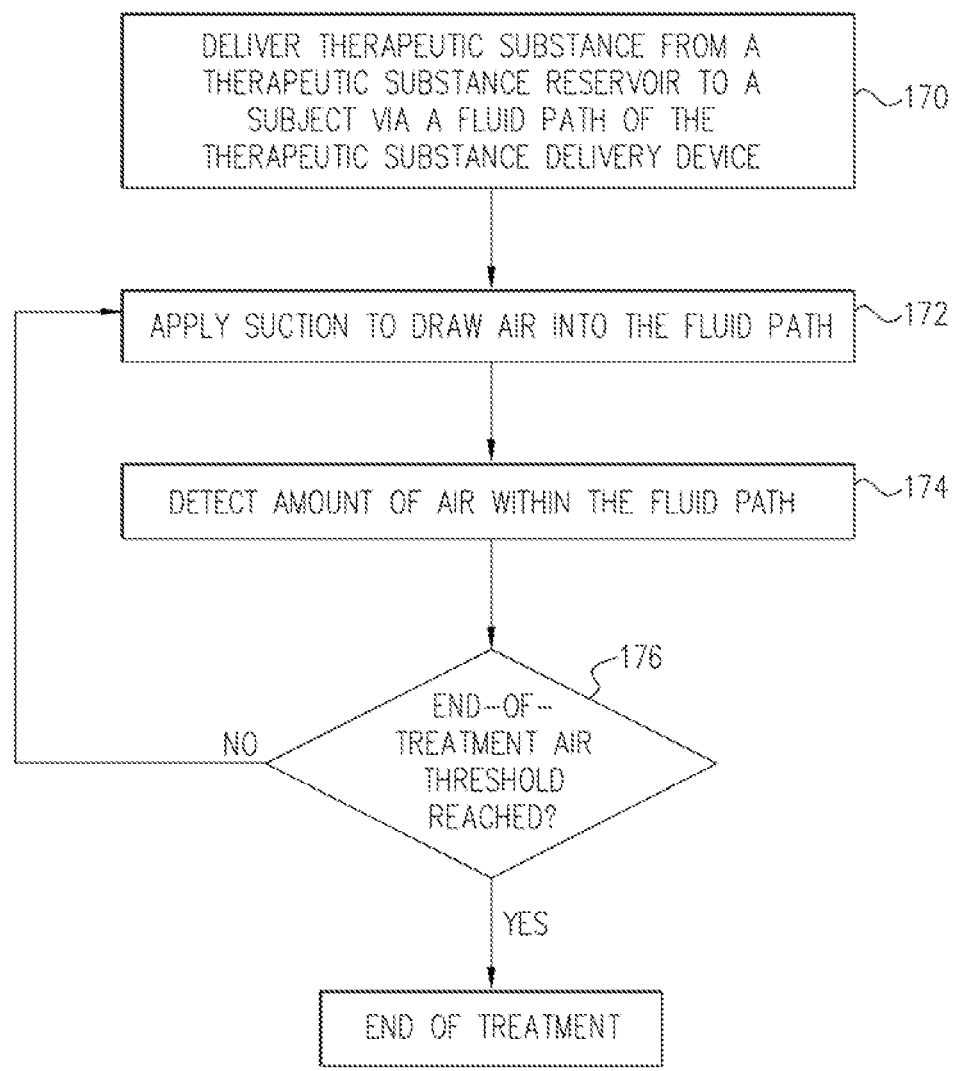
FIG. 13 is a flow chart depicting an end-of-treatment detection method, in accordance with some applications of the present invention.

Reference is now made to FIG. 13, which is a flow chart depicting an end of treatment detection method, in accordance with some applications of the present invention. In step 170, therapeutic substance is delivered from therapeutic substance reservoir 22, as described hereinabove. In step 172, the residual therapeutic substance within fluid path 26 is pumped to the subject by applying suction to draw the air into fluid path 26. For some applications, an air detector (such as for example, an air detector similar to air detector 152 in FIGS. 8-10, and FIG. 12) may be used to detect the air within fluid path 26 (step 174) as it is pumped to the subject. Typically, the amount of the residual air is larger than a typical air bubble which may be detected by the air detector during treatment. Thus, an end-of-treatment air threshold may be set (as depicted by decision diamond 176), such that if the amount of air within fluid path 26, detected by the air detector, reaches the end-of-treatment air threshold, it is an indication that the treatment has ended, i.e., all of the residual therapeutic substance within fluid path 26 has been delivered to the subject. The suction of air into the fluid path is then terminated. Typically, body needle injection mechanism 28 is then triggered to retract body needle 30 from the body of the subject and, optionally, reservoir needle 24 is retracted from therapeutic substance reservoir 22.

Alternatively, or additionally, at the end of a treatment, reservoir needle 24 may be retracted from therapeutic substance reservoir 22 (as described hereinabove). Once reservoir needle 24 has been retracted to within the sterile enclosure of therapeutic substance delivery device 20, sterile air may be pumped through the fluid line. For some applications, this method may be performed using a therapeutic substance delivery device other than therapeutic substance delivery device 20.

Figure 8:
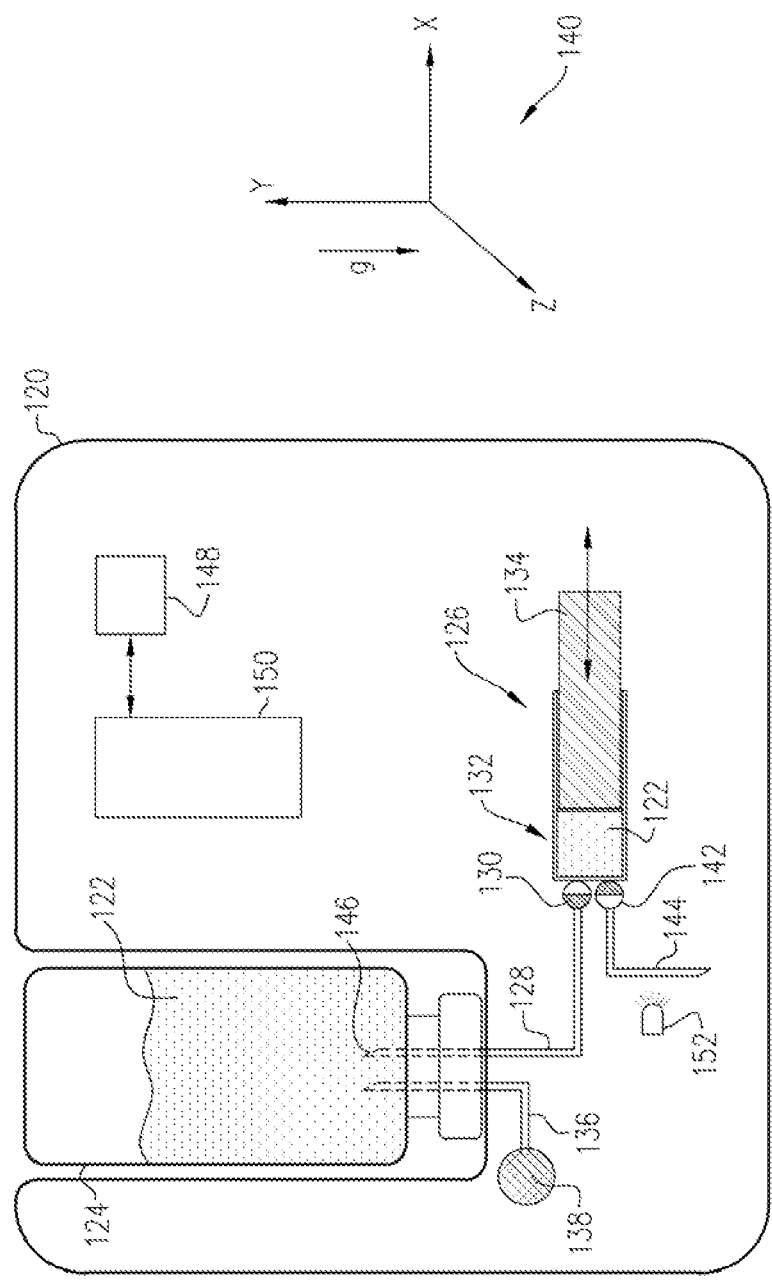
FIG. 8 is a schematic illustration of a therapeutic substance delivery device in accordance with some applications of the present invention.

Reference is now made to FIG. 8, which is a schematic illustration of a therapeutic substance delivery device 120, in accordance with some applications of the present invention. The therapeutic substance 122 is contained in a therapeutic substance reservoir 124, e.g., a non-collapsible container from which therapeutic substance 122 can be drawn without changing the internal dimensions of therapeutic substance reservoir 124, e.g., a vial. Therapeutic substance delivery device 120 may engage with standard commercially-available drug vials, such that a patient can simply insert the drug vial into therapeutic substance delivery device 120, without having to use an intermediary filling apparatus to transfer therapeutic substance 122 from the drug vial to therapeutic substance delivery device 120.

The coordinate system 140 is fixed with respect to therapeutic substance delivery device 120 and shows the direction of gravity g with respect to therapeutic substance delivery device 120. For some applications, reservoir 124 may be prefilled, e.g., by a pharmaceutical company. Alternatively, reservoir 124 may be filled by the subject prior to engagement with therapeutic substance delivery device 120. Therapeutic substance 122 is drawn out of reservoir 124 using a pump 126, e.g., an electromechanical pumping assembly such as electromechanical pumping assembly 32 as described hereinabove, that is driven by control circuitry 150.

Therapeutic substance 122 is drawn out of reservoir 124 through fluid intake path 128. Therapeutic substance 122 then flows through a first one-way valve 130 into a pump chamber 132. Pump chamber 132 typically has maximum internal dimensions that (i) are smaller than the internal dimensions of therapeutic substance reservoir 124. The volume of therapeutic substance 122 within pump chamber 132 varies in response to changes in the internal dimensions of pump chamber 132. That is, as the internal dimensions of pump chamber 132 increase, the volume of therapeutic substance 122 increases within pump chamber 132 increases accordingly, and as the internal dimensions of pump chamber 132 decrease the volume of therapeutic substance 122 decreases within pump chamber 132 decreases accordingly. For example, pump chamber 132 may be a syringe, and the internal dimensions may change as the plunger of the syringe is moved within the barrel of the syringe.

Typically, therapeutic substance 122 is drawn out of therapeutic substance reservoir 124 by moving a plunger 134, disposed within pump chamber 132, backwards, thereby increasing the internal dimensions of the pump chamber 132. While therapeutic substance 122 is drawn out of reservoir 124, vacuum builds within reservoir 124, causing air to enter reservoir 124 through an air path 136. For some applications, the air first passes through a hydrophobic filter 138. Hydrophobic filter 138 prevents therapeutic substance 122 from passing out, while allowing sterile air from inside therapeutic substance delivery device 120 to enter reservoir 124.

When plunger 134 is finished moving backward (positive x-direction of coordinate system 140) the drawing of therapeutic substance 122 from the reservoir 124 stops. After pump chamber 132 is full of therapeutic substance 122, plunger 134 is driven to move in the opposite direction (negative x-direction of coordinate system 140), and therapeutic substance 122 is pushed out through a second one-way valve 142 and delivered to the subject through a fluid exit path 144.

As shown in FIG. 8, the orientation of therapeutic substance delivery device 120 is such that gravity g is pulling therapeutic substance 122 downwards and an end 146 of fluid intake path 128 is immersed in therapeutic substance 122 within reservoir 124. Drawing therapeutic substance 122 out of reservoir 124 is only possible as long as end 146 of fluid intake path 128 is immersed in therapeutic substance 122. Therefore, drawing therapeutic substance 122 out of reservoir 124 depends on the direction of gravity g with respect to therapeutic substance delivery device 120.

Figure 9:
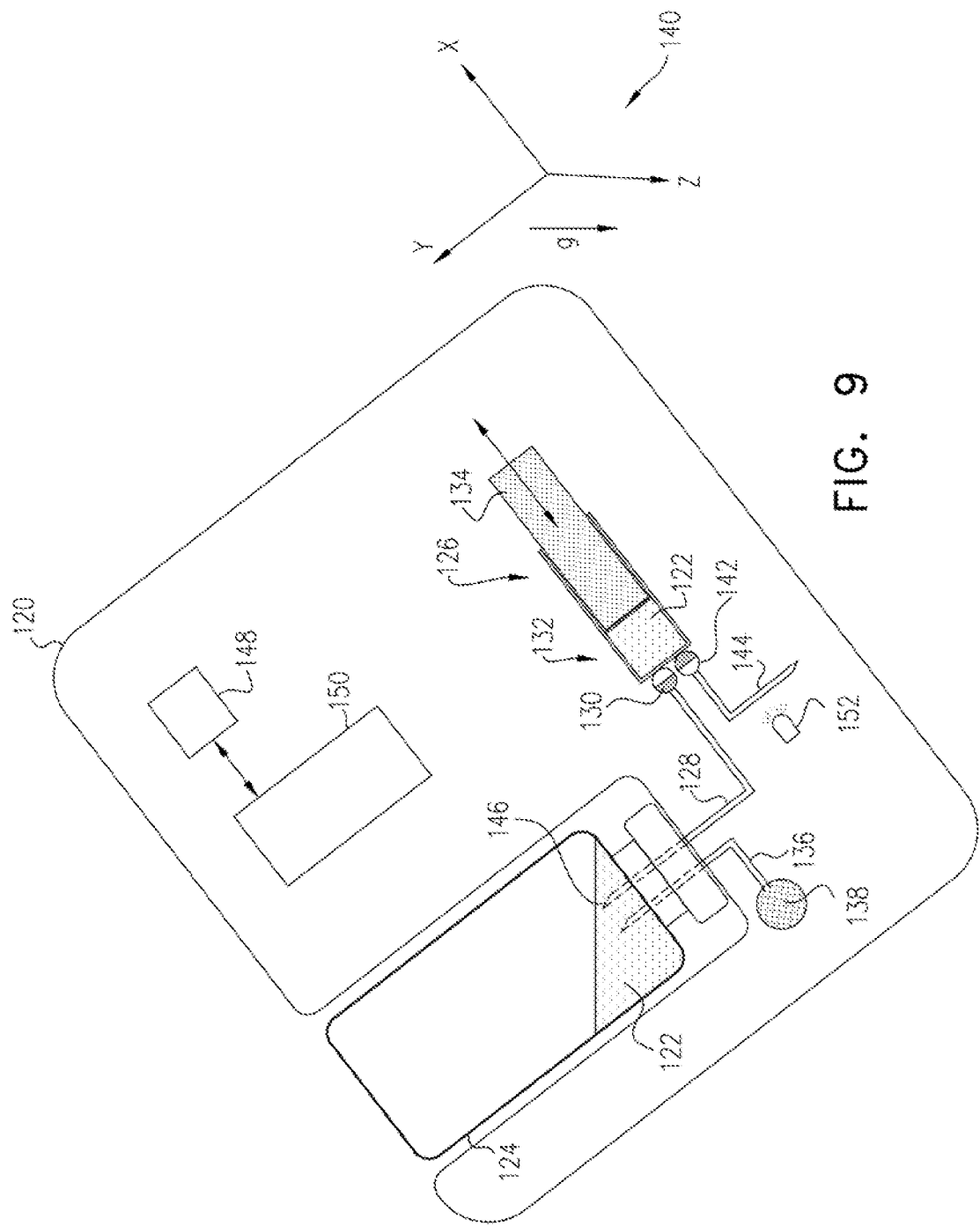
FIGS. 9-10 are schematic illustrations of the therapeutic substance delivery device of FIG. 8 in a different orientation with respect to gravity, in accordance with some applications of the present invention.

Reference is now made to FIG. 9, which is a schematic illustration of therapeutic substance 122 in a different orientation with respect to gravity g in accordance with some applications of the present invention. The volume of therapeutic substance 122 within reservoir 124 has dropped as well. For example, the scenario depicted in FIG. 9 may occur towards the end of a therapeutic substance treatment. As the volume of therapeutic substance 122 drops due to therapeutic substance 122 being pumped out of reservoir 124, end 146 of fluid intake path 128 is becoming closer to the air inside reservoir 124. Additionally, a tilt of therapeutic substance delivery device 120 in any plane will change the disposition of therapeutic substance 122 within reservoir 124 due to gravity g, thus changing the possible distance between end 146 of fluid intake path 128 and air within reservoir 124. Typically, fluid intake path 128 is centered with respect to reservoir 124 (as shown in FIGS. 8, 9, 10, and 12), in order to maximize the distance between end 146 of fluid intake path 128 and air within reservoir 124 for a range of orientations of therapeutic substance delivery device 120.

Thus, two parameters affecting when therapeutic substance 122 can be drawn out of reservoir 124 are (i) the orientation of reservoir 124 with respect to gravity g, i.e., the orientation of therapeutic substance delivery device 120 with respect to gravity g, and (ii) the volume of therapeutic substance 122 within reservoir 124.

Figure 10:
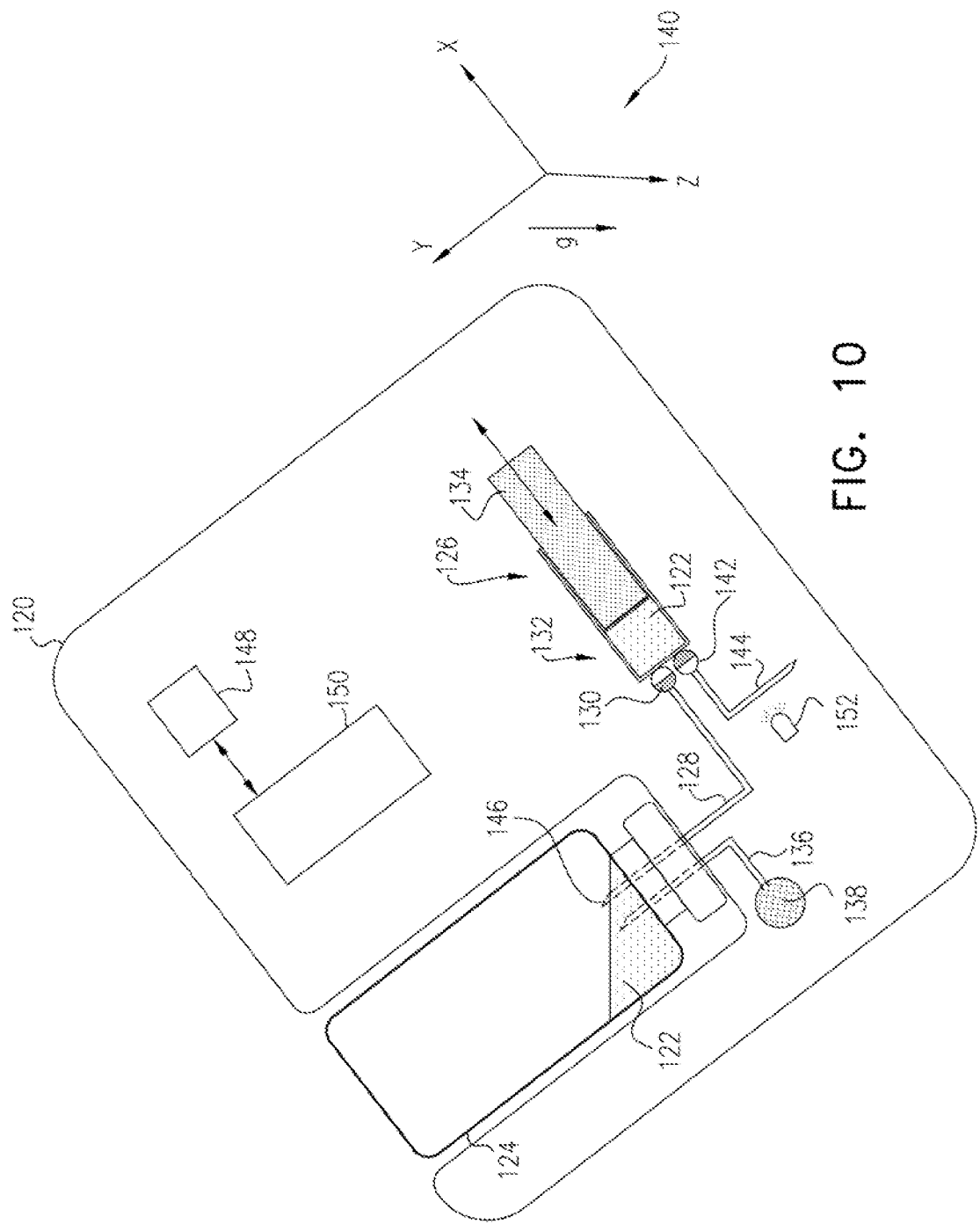

Reference is now made to FIG. 10, which is a schematic illustration of therapeutic substance delivery device 120 shown in the same orientation with respect to gravity g as in FIG. 9, but with a lower volume of therapeutic substance 122 remaining within reservoir 124. End 146 of fluid intake path 128 is exposed to air within reservoir 124. If plunger 134 is drawn backwards in this scenario, air will flow into pump chamber 132 instead of therapeutic substance 122.

Typically, a three-dimensional orientation sensor 148, e.g., an accelerometer or a gyroscope, monitors the orientation of therapeutic substance delivery device 120 with respect to gravity g. Orientation sensor 148 generates an output to control circuitry 150 that is indicative of the orientation of therapeutic substance delivery device 120 with respect to gravity g.

Additionally, the motion of pump 126 is translated into a volume of therapeutic substance 122 pumped from reservoir 124. For example, control circuitry 150 calculates a volume of therapeutic substance 122 that will be remaining in reservoir 124 after each drawing of therapeutic substance 122 into pump chamber 132. For some applications, if control circuitry 150 determines that drawing enough therapeutic substance 122 to fill pump chamber 132 will leave end 146 of fluid intake path 128 exposed to air, control circuitry 150 may drive pump 126 to only partially fill pump chamber 132 so as to avoid end 146 being exposed to air within therapeutic substance reservoir 124.

Using the two above-described parameters, control circuitry 150 determines whether end 146 of fluid intake path 128 is immersed in therapeutic substance 122 or exposed to air within reservoir 124. When end 146 of fluid intake path 128 is immersed in therapeutic substance 122, control circuitry 150 drives pump 126 to fill pump chamber 132 with therapeutic substance 122. Control circuitry 150 drives pump 126 to push therapeutic substance 122 out through fluid exit path 144 to the subject. As used hereinbelow, a "good position" of therapeutic substance delivery device 120 refers to a position in which end 146 of fluid intake path 128 is immersed in therapeutic substance 122 at the end of an intake cycle, i.e., after therapeutic substance 122 is drawn into pump chamber 132.

Typically, the cycle of drawing therapeutic substance 122 from reservoir 124 is not a constant cycle and is not dependent on a predetermined treatment schedule. When reservoir 124 is determined to contain less than a given amount of therapeutic substance 122, e.g., when therapeutic substance reservoir 124 is less than 50% full of therapeutic substance 122, therapeutic substance delivery device 120 starts to check if end 146 of fluid intake path 128 is exposed to air or immersed in therapeutic substance 122. If end 146 of fluid intake path 128 is immersed in therapeutic substance 122, pump 126 draws therapeutic substance 122 from reservoir 124 into pump chamber 132 until pump chamber 132 is full again (when control circuitry 150 determines that filling pump chamber 132 will leave end 146 still immersed in therapeutic substance 122), or until the distance between end 146 and air within reservoir 124 decreases below a threshold distance. The threshold distance (e.g., for a 10 ml vial) is typically at least 0.1 mm (e.g., at least 0.5 mm), and/or less than 5 mm. For example, the threshold distance may be 0.1-5 mm, e.g., 0.5-5 mm. Threshold distances for larger or smaller vials (e.g., 0.5 ml, 1 ml, 2 ml, 5 ml, 10 ml, 20 ml, 30 ml, 50 ml, 100 ml) typically vary linearly to these ranges. Even if pump 126 had been in the middle of a delivery phase where plunger 134 moves incrementally forward (negative x-direction of coordinate system 140), pump 126 typically switches the direction of motion of plunger 134 (to positive x-direction of coordinate system 140) in order to refill pump chamber 132. Thus, pump 126 maintains pump chamber 132 full of fluid by refilling it generally whenever a "good position" of therapeutic substance delivery device 120 is detected. Typically, the changes in orientation of therapeutic substance delivery device 120 are due to position changes of the patient wearing therapeutic substance delivery device 120.

For some applications, if end 146 of fluid intake path 128 is exposed to air within reservoir 124, pump 126 keeps pumping therapeutic substance 122 through fluid exit path 144, while control circuitry 150 constantly monitors the volume of therapeutic substance 122 remaining in reservoir 124 and the orientation of therapeutic substance delivery device 120, "looking" for the right timing to drive pump 126 to change the direction of plunger 134 and refill pump chamber 132. Typically, the time it takes pump 126 to refill pump chamber 132 is substantially smaller than the time it takes to deliver the contents of pump chamber 132 to the subject. Thus, refilling pump chamber 132 whenever a "good position" is detected, and not only in response to pump chamber 132 being empty, i.e., having a non-constant refilling cycle that is determined in real time by control circuitry 150, allows the system to maintain continuity of flow while reducing the number of times during the treatment where the subject may have to change position (as described hereinbelow) in order for therapeutic substance delivery device 120 to refill pump chamber 132 and continue treatment.

For some applications, in the event that a "good position" of therapeutic substance delivery device 120 does not occur during the entire duration of pump chamber 132 being emptied, control circuitry 150 generates an alert. The alert may be, for example, an audible alert, visual alert, verbal alert, or vibration. In response to the alert, the subject is instructed to change position in order to reorient therapeutic substance delivery device 120 with respect to gravity so that pump chamber 132 can be refilled and treatment can continue.

A benefit of the above-described non-constant refilling cycle is that, in particular during a relatively longer treatment (e.g., above 1 hour), there is no need to have therapeutic substance delivery device 120 in a "good position" for refilling during the entire duration of the treatment. For some applications, even in short treatments where the patient may be asked to maintain therapeutic substance delivery device 120 in a "good position" during the duration of the treatment, air within fluid exit path 144 may be detected, as further described hereinbelow, in order to reduce possible errors in delivery of therapeutic substance 122.

Below are two examples using the same system which includes a 10 ml therapeutic substance reservoir 124 and a pump having a 0.25 ml pump chamber 132, which can be filled in 5 seconds.

Case 1: Pump 126 is programmed to deliver therapeutic substance 122 at a rate of 60 ml/h. The treatment takes 10 minutes and requires 40 intakes of therapeutic substance 122 from reservoir 124 to pump chamber 132. Pump chamber 132 takes 10 seconds to empty and 5 seconds to fill, resulting in a total of 15 seconds per full cycle. Thus, for such short treatments (e.g., 10 minutes) where refilling of pump chamber 132 occurs very often, the patient should be instructed to maintain therapeutic substance delivery device 120 positioned in a "good position" for refilling during the length of the treatment, i.e., during the entire 10 minutes. Possible errors in the volume of therapeutic substance 122 delivered to the patient during treatment may be reduced by detecting the presence of air in fluid exit path 144, as described hereinbelow.

Case 2: Pump 126 is programmed to deliver therapeutic substance 122 at a rate of 0.25 ml/h, setting the total treatment time to 40 hours. In this case, to refill and subsequently empty the pump chamber 132 takes 1 hour (the drawing of therapeutic substance 122 into pump chamber 132 is still only 5 seconds). For the therapeutic substance delivery device 120, which is typically a wearable patch pump, to be in a "good position" for refilling during the entire 40 hours is impractical (because the patient may be in many different positions during this time). Therefore, using the above-described non-constant refilling cycle allows the system to require a "good position" with respect to gravity g for only a few seconds every 1 hour. Control circuitry 150 starts monitoring for a "good position" after 50% of reservoir 124 has been emptied. In this case, the therapeutic substance delivery device 120 needs to be in a "good position" for refilling for only 5 seconds every 1 hour. This allows the patient to behave normally, with limited restrictions, e.g., the patient may even go to sleep during the treatment, depending on the orientation of substance delivery device 120 on the patient's body and/or based on substance delivery device 120 generating the above-described alerts, as appropriate.

For some applications, if for any reason an incorrect determination is made with regards to the exposure of end 146 of fluid intake path 128 to air, and air is drawn into pump chamber 132, an air detector 152 detects the air in fluid exit path 144. Typically, the amount of air detected is calculated by control circuitry 150. For some applications, if less than a threshold amount of air is detected, control circuitry 150 continues to drive pump 126 to deliver therapeutic substance 122 to the subject without any interruptions. Alternatively, if more than the threshold amount of air is detected, control circuitry 150 may perform a compensatory calculation so as to avoid errors in the volume of therapeutic substance 122 being delivered to the subject (i.e., the air accidentally pumped into pump chamber 132 is discounted from the volume of therapeutic substance 122 within reservoir 124, and the volume of therapeutic substance 122 pumped from reservoir 124 is corrected, allowing the system to maintain the right delivery of fluid as preprogrammed).

For some applications, an air-limit threshold may be set such that if the amount of air detected is above the air-limit threshold, pump 126 is paused until a "good position" of therapeutic substance delivery device 120 is achieved.

Reference is again made to FIG. 13. Similarly to as described hereinabove with reference to therapeutic substance delivery device 20, subsequently to all of therapeutic substance 122 being delivered from reservoir 124 (step 170 of FIG. 13), control circuitry 150 may drive therapeutic substance delivery device 120 to continue pumping so as to delivery any residual therapeutic substance 122 remaining within the fluid path, e.g., fluid intake path 128 and/or fluid exit path 144, to the patient, thereby reducing dead volume. Due to air entering reservoir 124 through air path 136 as pump 126 pumps from reservoir 124, there is a continuous supply of air that can be pumped through the fluid path at the end of the treatment (step 172 of FIG. 13). For some applications, an end-of-treatment air threshold is set such that when air within fluid exit path 144, detected by air detector 152 (step 174 of FIG. 13), reaches the end-of-treatment air threshold (as depicted by decision diamond 176 of FIG. 13), it is an indication that the treatment has ended, i.e., all of residual therapeutic substance 122 remaining within the fluid path has been delivered to the subject.

Figure 11:
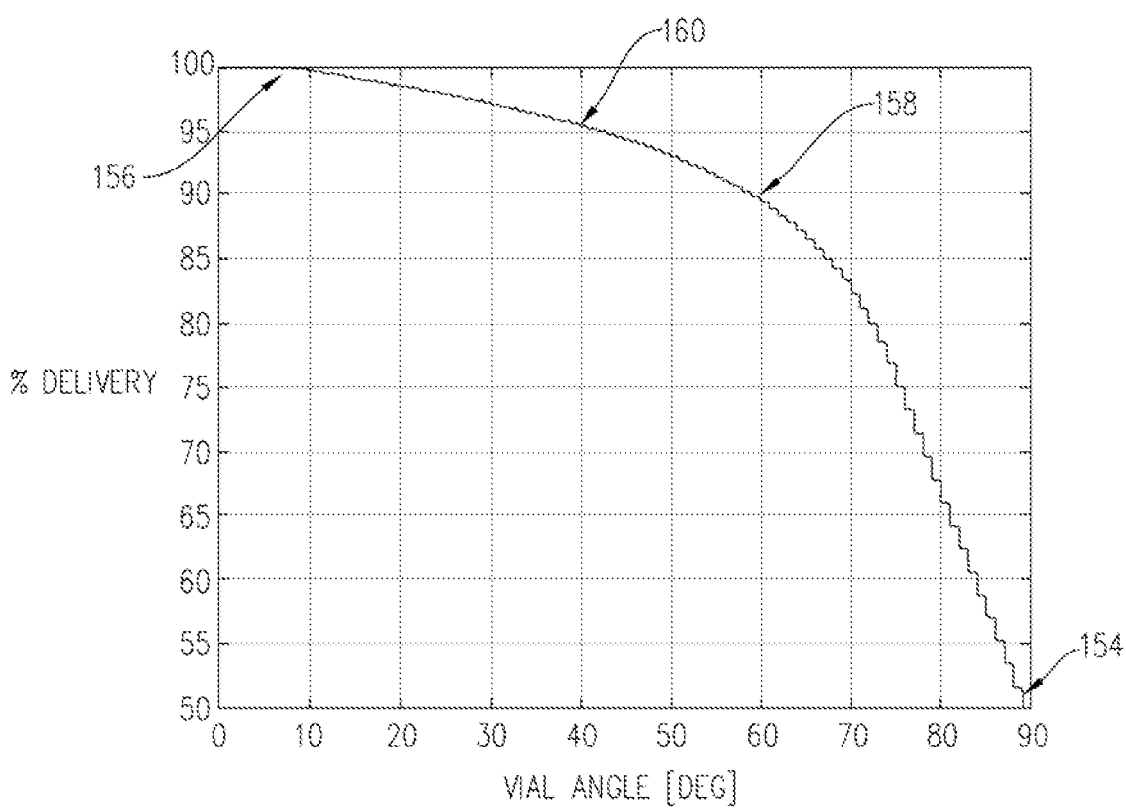
FIG. 11 is a graph showing percentage of therapeutic substance delivered versus an angle of the therapeutic substance delivery device, in accordance with some applications of the present invention.

Reference is now made to FIG. 11, which is a graph showing different percentages of therapeutic substance 122 delivered from a reservoir 124 versus corresponding angles of reservoir 124 (with respect to the direction of gravity g), above which therapeutic substance 122 cannot be drawn from reservoir 124. The graph is presented by way of example and shows data for a particular example using a reservoir 124 which holds 10 ml of therapeutic substance 122. The length of fluid intake path 128 within reservoir 124 (i.e., how far fluid intake path 128 extends into reservoir 124) is taken into account as well. When around 50% of therapeutic substance 122 has been delivered, marked by arrow 154 on the graph, reservoir 124 may be at any angle from zero degrees to 90 degrees with respect to the direction of gravity g, even substantially horizontal with respect to the direction gravity g (which corresponds to 90 degrees on the graph). Thus, at any angle from 0 to 90 degrees, therapeutic substance delivery device 120 is in a good position to fill pump chamber 132 (i.e., end 146 of fluid intake path 128 is immersed in therapeutic substance 122 such that at any angle from 0-90 degrees, pump chamber 132 can be filled without exposing end 146 to air). As more therapeutic substance 122 is delivered from reservoir 124, a respectively smaller angle with respect to the direction of gravity g is required in order for end 146 of fluid intake path 128 to be immersed in therapeutic substance 122 and not exposed to air. Changes in the internal dimensions of reservoir 124, the volume of therapeutic substance 122 within reservoir 124, and the length of fluid intake path 128 within reservoir 124 will affect calculations of which angles result in a "good position" of therapeutic substance delivery device 120.

Typically, most of therapeutic substance 122 can be delivered from reservoir 124 to the subject without any special orientation requirements. At 60 degrees with respect to the direction of gravity g, marked by arrow 158, up to 90% of therapeutic substance 122 in reservoir 124 can be delivered to the patient, which is typically 95% of the dose. At 41 degrees with respect to the direction of gravity g, marked by arrow 160, up to 95% of therapeutic substance 122 in reservoir 124 can be delivered to the subject, which is typically 100% of the dose.

Reference is now made to FIG. 12, which is a schematic illustration of therapeutic substance delivery device 120 with a different mechanism allowing air to enter reservoir 124, in accordance with some applications of the present invention. Pump 126 contains pump chamber 132 and an air chamber 162. Plunger 134 moves back and forth between pump chamber 132 and air chamber 162. As the volume of therapeutic substance 122 in pump chamber 132 decreases when plunger 134 moves in the negative x-direction, i.e., during delivery of therapeutic substance 122 to the subject, the volume of air in air chamber 162 increases by the same amount. During this increase of the volume of air in air chamber 162, sterile air from within therapeutic substance delivery device 120 is sucked into air chamber 162 through an air intake path 164 and a third one-way valve 166. As the volume of therapeutic substance 122 in pump chamber 132 increases when plunger 134 moves in the positive x-direction, i.e., during the drawing of therapeutic substance 122 from reservoir 124 into pump chamber 132, the air inside air chamber 162 is pushed through a fourth one-way valve 168 and air path 136 into reservoir in order to prevent vacuum building up within reservoir 124.

Reference is now made to FIGS. 14A-B, 15A-B, 16A-B, 17A-B, and 18A-B, which depict therapeutic substance delivery device 120 along with a plurality of internal mechanisms, which, except where indicated otherwise, operate in the same way, mutatis mutandis, as the internal mechanisms of therapeutic substance delivery device 20, as described hereinabove with reference to FIGS. 1A-C, 2A-C, 3A-B, 4A-B, and 5A-B.

Figure 14A:
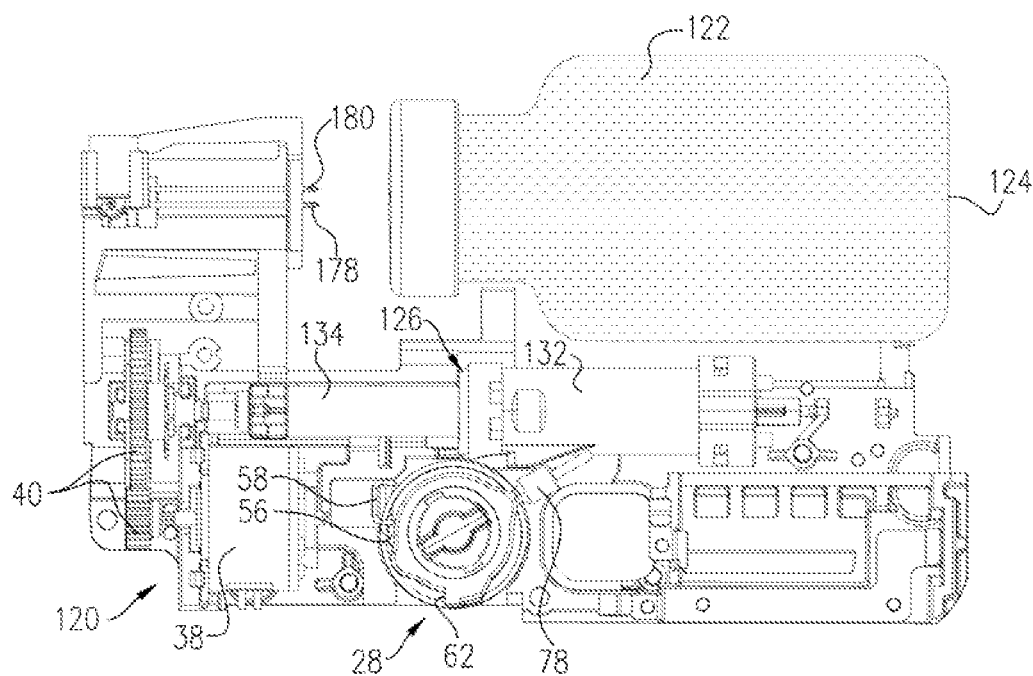
FIGS. 14A-B are schematic illustrations of different perspectives of a therapeutic substance delivery device showing a plurality of internal mechanisms at their respective start positions, in accordance with some applications of the present invention.
Figure 14B:
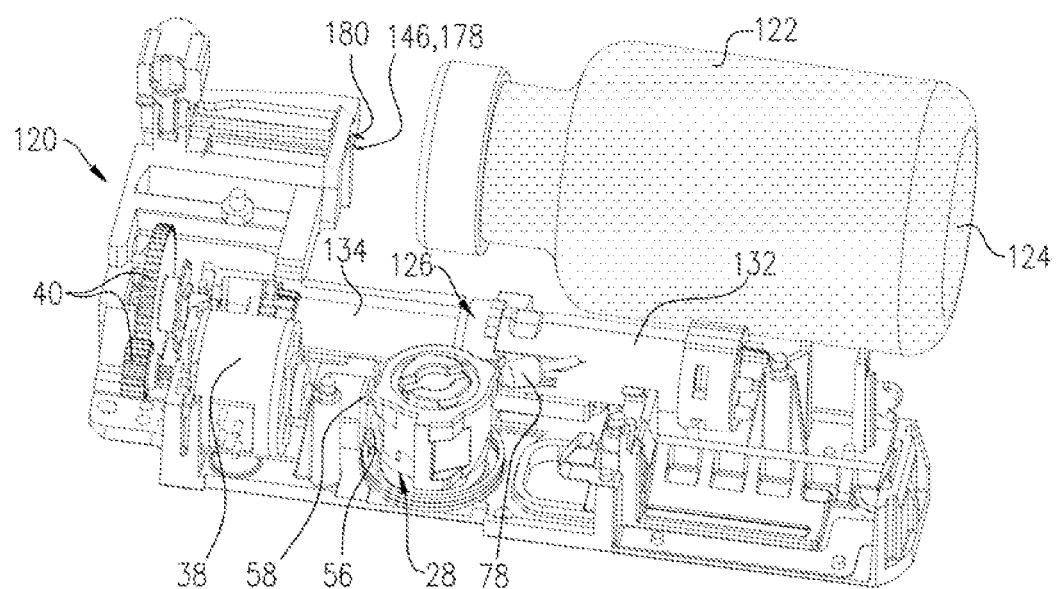

Reference is now made to FIGS. 14A-B, which are schematic illustrations of different perspectives of therapeutic substance delivery device 120 showing the plurality of internal mechanisms in their respective start positions, in accordance with some applications of the present invention. As described hereinabove with reference to FIGS. 8-12, therapeutic substance delivery device 120 engages with therapeutic substance reservoir 124, e.g., a non-collapsible container from which therapeutic substance 122 can be drawn without changing the internal dimensions of therapeutic substance reservoir 124, e.g., a vial. Therapeutic substance reservoir 124 may be prefilled, or alternatively, may be fillable by the user. Therapeutic substance reservoir 124 may be replaceable.

As described hereinabove with reference to FIGS. 8-12, therapeutic substance delivery device 120 has (a) fluid intake path 128 and (b) an air path 136. Similarly to as described hereinabove with reference to therapeutic substance delivery device 20, fluid intake path 128 typically has a reservoir needle 178 at an upstream end of fluid intake path 128. End 146 of fluid intake path 128, described hereinabove, is typically the tip of reservoir needle 178. Reservoir needle 178 is positioned to penetrate therapeutic substance reservoir 124 (such as is further described hereinbelow with reference to FIGS. 15A-B). Air path 136, which draws sterile air from within therapeutic substance delivery device 120 into therapeutic substance reservoir 124, typically has an air needle 180 at a downstream end of air path 136. Air needle 180 is positioned to penetrate therapeutic substance reservoir 124 along with reservoir needle 178 (such as is further described hereinbelow with reference to FIGS. 15A-B).

Body needle injection mechanism 28 as shown in FIGS. 14A-B, 15A-B, 16A-B, 17A-B, and 18A-B is the same body needle injection mechanism as described hereinabove with reference to therapeutic substance delivery device 20, and operates in the same manner. Body needle 30 is disposed at a downstream end of fluid exit path 144 of therapeutic substance delivery device 120.

Pump 126 within therapeutic substance delivery device 120 is typically an electromechanical pumping assembly, such as electromechanical pumping assembly 32 described hereinabove. Pump 126 is shaped to define a pump chamber 132 and comprises a plunger 134 disposed within pump chamber 132. As further described hereinbelow, plunger 134 moves back and forth through the same plurality of discrete motion phases as plunger 36, described hereinabove with respect to therapeutic substance delivery device 20, and accordingly, each motion phase of plunger 134 activates an operation of therapeutic substance delivery device 120. Typically, motor 38 drives the motion of plunger 134 via a series of gears 40, one of which is coupled to a screw that is coaxial with plunger 134 so as to translate rotational motion of gears 40 into linear motion of plunger 134.

The operations of therapeutic substance delivery device 120 typically include driving reservoir needle 178 and air needle 180 to penetrate therapeutic substance reservoir 124, advancing body needle 30 into the body of the subject, withdrawing therapeutic substance 122 from therapeutic substance reservoir 124, pumping therapeutic substance 122 into the subject, and retracting body needle 30 from the body of the subject (or a subset of these operations). Optionally, the plurality of operations may further include retracting reservoir needle 178 and air needle 180 from therapeutic substance reservoir 124.

For some applications, the operations are activated in a sequence as will be described hereinbelow with reference to motion phases 1-4 of the plunger's motion. The sequence of operations, however, is not limiting, and the operations may be activated by the plunger's motion in any sequence. For some applications, only some, e.g., two or three, of the operations may be activated by the motion of the plunger.

Figure 15A:
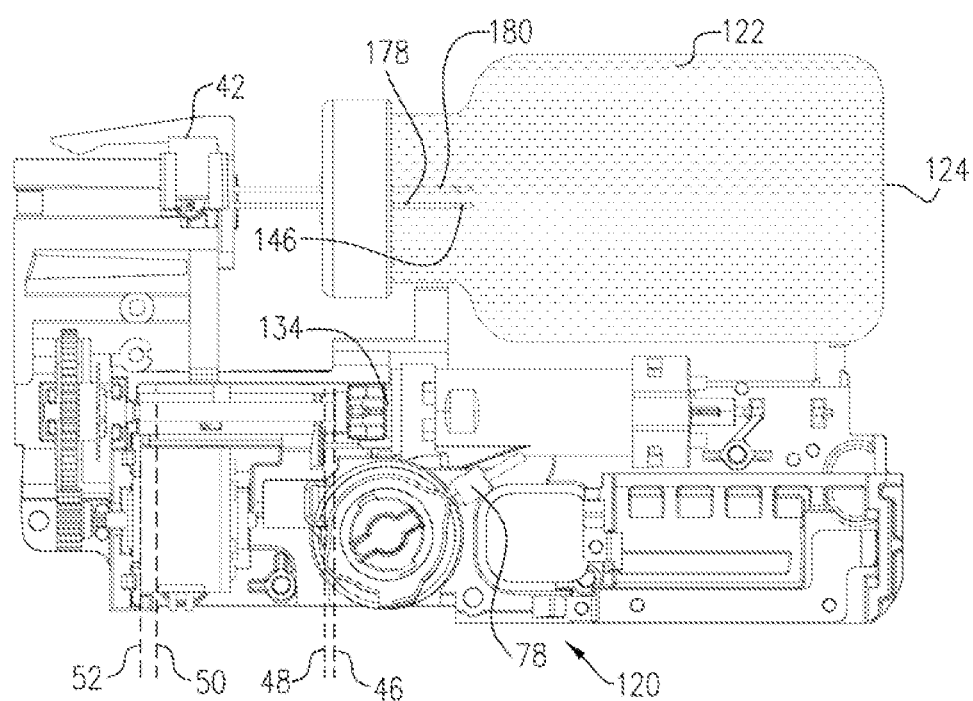
FIGS. 15A-B are schematic illustrations of different perspectives of the therapeutic substance delivery device of FIGS. 14A-B and a reservoir needle and an air needle after a first motion phase of a plunger, in accordance with some applications of the present invention.
Figure 15B:
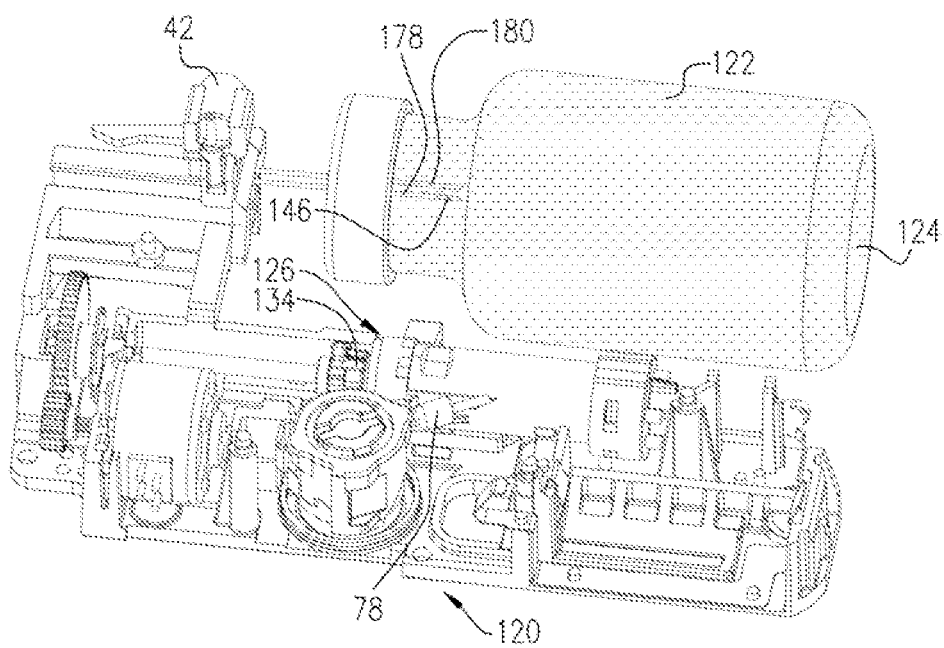

Reference is now made to FIGS. 15A-B, which are schematic illustrations of different perspectives of therapeutic substance delivery device 120 and of reservoir needle 178 and air needle 180 after a first motion phase of plunger 134. Typically, the first motion phase of plunger 134 is a maximal advance of plunger 134 in a first direction to drive reservoir needle 178 and air needle 180 to penetrate therapeutic substance reservoir 124. Reservoir needle 178 and air needle 180 are driven to penetrate reservoir 124, and optionally to be retracted from reservoir 124, in the same manner as described hereinabove with reference to reservoir needle 24 of therapeutic substance delivery device 20 in FIGS. 2A-C. Typically, both reservoir needle 178 and air needle 180 are mounted on needle slider 42. After the maximal advance of plunger 134, reservoir needle 178 and air needle 180 are in fluid communication with therapeutic substance 122 within reservoir 124.

It is noted that dashed lines 46, 48, 50, and 52 as shown in FIGS. 15A, 16A, 17A, and 18A represent the same points to which the plunger may advance or retract during the various motion phases as their correspondingly numbered dashed lines in FIGS. 2A, 3A, 4A, and 5A.

Figure 16A:
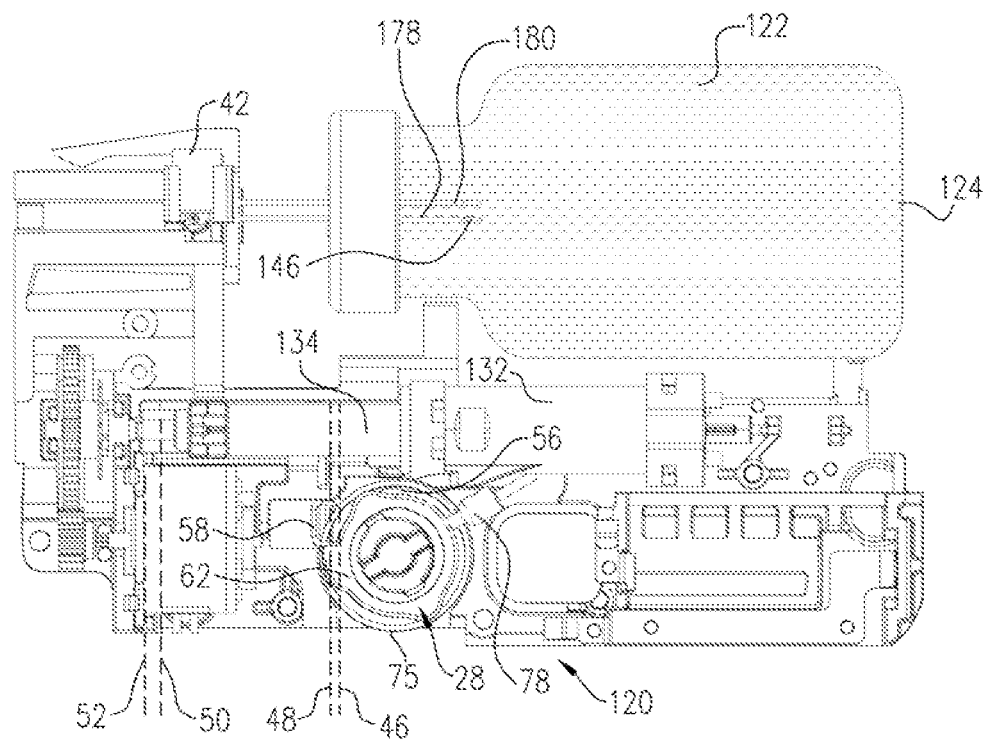
FIGS. 16A-B are schematic illustrations of different perspectives of the therapeutic substance delivery device of FIGS. 14A-B, showing a second motion phase of the plunger and a body needle injection mechanism rotating to drive a body needle into the body of a subject, in accordance with some applications of the present invention.
Figure 16B:
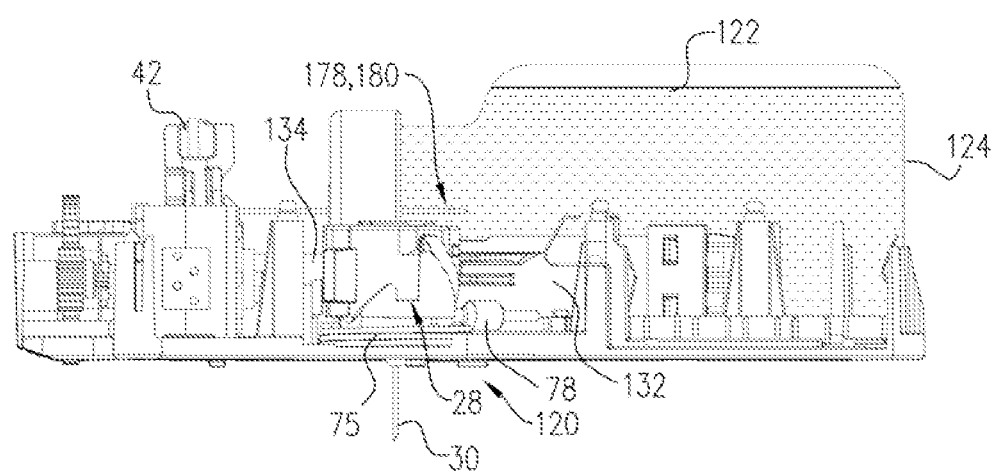

Reference is now made to FIGS. 16A-B, which are schematic illustrations of different perspectives of therapeutic substance delivery device 120 showing a second motion phase of plunger 134 and body needle injection mechanism 28 rotating to drive body needle 30 into the body of the subject, in accordance with some applications of the present invention. Just as described hereinabove with reference to the second motion phase of plunger 36, typically, the second motion phase of plunger 134 is a partial retraction of plunger 134 which causes body needle injection mechanism 28 to advance body needle 30 into the body of the subject. Typically, the partial retraction of plunger 134 is less than a maximal retraction of plunger 134 in the second direction. Dashed line 50 indicates a stopping point of plunger 134 after the partial retraction. Since reservoir needle 178 already penetrated therapeutic substance reservoir 124 during the first motion phase, a fluid connection is established between pump chamber 132 and therapeutic substance reservoir 124. Therefore, it follows that as plunger 134 retracts from within pump chamber 132 during the second motion phase, therapeutic substance 122 is drawn into pump chamber 132 via reservoir needle 178 and fluid intake path 128.

As therapeutic substance 122 is drawn from reservoir 124, air is drawn into reservoir 124. Typically, sterile air is drawn from within therapeutic substance delivery device 120 into reservoir 124 through air path 136 and hydrophobic filter 138 (as described with reference to FIGS. 8-10), and enters reservoir 124 through air needle 180.

It is noted that body needle injection mechanism 28 as shown in FIGS. 14A-B, 15A-B, 16A-B, 17A-B, and 18A-B, is the same mechanism and operates in the same manner as body needle injection mechanism 28 described hereinabove with reference to FIGS. 3A-B, 5A-B, and 6A-C.

Figure 17A:
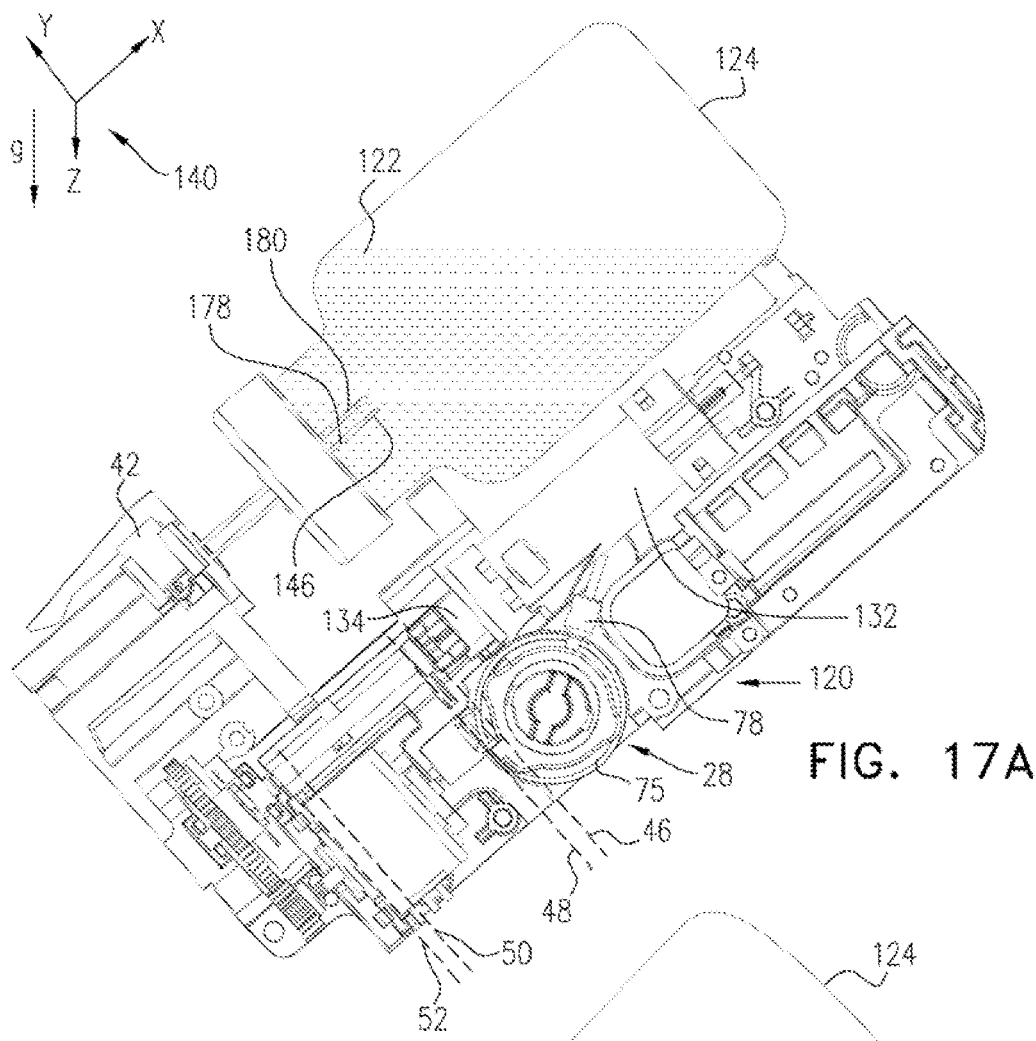
FIGS. 17A-B are schematic illustrations of different perspectives of the therapeutic substance delivery device of FIGS. 14A-B, showing a third motion phase of the plunger, in accordance with some applications of the present invention.
Figure 17B:
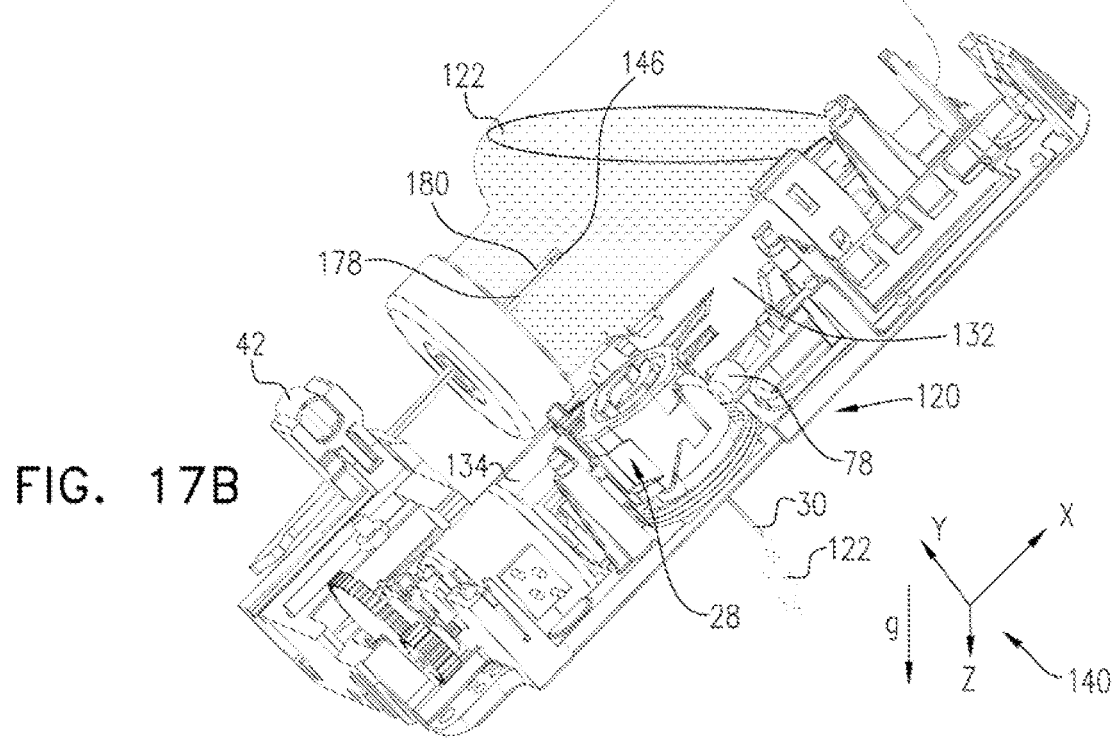

Reference is now made to FIGS. 17A-B, which are schematic illustrations of different perspectives of therapeutic substance delivery device 120, showing a third motion phase of plunger 134, in accordance with some applications of the present invention. Just as described hereinabove with reference to the second motion phase of plunger 36, typically, the third motion phase of plunger 134 is a partial advance of plunger 134 in the first direction in order to pump therapeutic substance 122 within pump chamber 132 to the subject via fluid exit path 144 and body needle 30. Dashed line 48 illustrates a stopping point of plunger 134 after plunger 134 has partially advanced in the first direction during the third motion phase.

The order of the motion phases of plunger 134 is typically the same as described hereinabove with reference to plunger 36 of therapeutic substance delivery device 20, including the reciprocating repetition of the second and third motion phases so as to repeatedly withdraw therapeutic substance 122 from reservoir 124 and into pump chamber 132 and pump it from pump chamber 132 to the subject. However, as described hereinabove with reference to FIGS. 9 and 10, a tilt of therapeutic substance delivery device 120 in any plane will change the disposition of therapeutic substance 122 within reservoir 124 due to gravity g, thus changing the possible distance between end 146 of reservoir needle 178 and air within reservoir 124. Thus, control circuitry 150 may actuate the non-constant refilling cycle described hereinabove. For example, when a "good position" of therapeutic substance delivery device 120 has been detected, control circuitry 150 may override the reciprocating pattern of the motion phases of plunger 134 that actuate, respectively, (a) drawing therapeutic substance 122 from reservoir 124 into pump chamber 132, e.g., the second motion phase, and (b) pumping therapeutic substance 122 from pump chamber 132 to the subject, e.g., the third motion phase, in order to cause plunger 134 to repeat the motion phase of partial retraction of plunger 134 in order to draw therapeutic substance 122 into pump chamber 132. For example, control circuitry 150 may drive pump 126 to interrupt the third motion phase of the plunger, i.e., to interrupt the operation of pumping therapeutic substance 122 to the subject, by repeating the second motion phase of the plunger, i.e., by repeating the operation of drawing therapeutic substance 122 from reservoir 124 to pump chamber 132.

Additionally, due to the detected orientation of therapeutic substance delivery device 120 and the volume of therapeutic substance 122 remaining in reservoir 124 at the end of any given pumping cycle, there may be repetitions of the second motion of plunger 134 in which plunger 134 does not retract all the way until dashed line 50. Pump 126 draws therapeutic substance 122 from reservoir 124 into pump chamber 132:

(a) until pump chamber 132 is full again, by retraction of plunger 134 all the way until dashed line 50 (this will occur when control circuitry 150 determines that filling pump chamber 132 will leave end 146 of reservoir needle 178 still immersed in therapeutic substance 122), or (b) until the distance between end 146 and air within reservoir 124 decreases below a threshold distance, by retraction of plunger 134 to a point that is in between dashed lines 50 and 48.

FIGS. 17A-B show therapeutic substance delivery device 120 in a "good position," in which end 146 of reservoir needle 178 is immersed in therapeutic substance 122, and plunger 134 may be subsequently retracted to dashed line 50, or to a point between dashed lines 50 and 48 as determined by control circuitry 150 in order to draw more therapeutic substance 122 into pump chamber 132. Additionally, since control circuitry 150 may override the repetitive cycle of the second and third motion phases, there may also be repetitions of the third motion phase, i.e., partial advance of plunger 134 to drive therapeutic substance 122 to the subject, in which plunger 134 does not reach dashed line 48, but stops short of dashed line 48 due to control circuitry 150 determining that the second motion phase should be actuated to draw more therapeutic substance 122 into pump chamber 132 due to the "good position" of therapeutic substance delivery device 120.

As described hereinabove with respect to the second and third motion phases of plunger 36 of therapeutic substance delivery device 20, avoiding a maximal advance and a maximal retraction of plunger 134 during the reciprocating motion of repeatedly withdrawing therapeutic substance 122 from reservoir 124 and pumping it to the subject allows plunger 134 to repeatedly retract and advance without causing activation of other operations which may occur when plunger 134 performs a maximal advance or a maximal retraction.

Figure 18A:
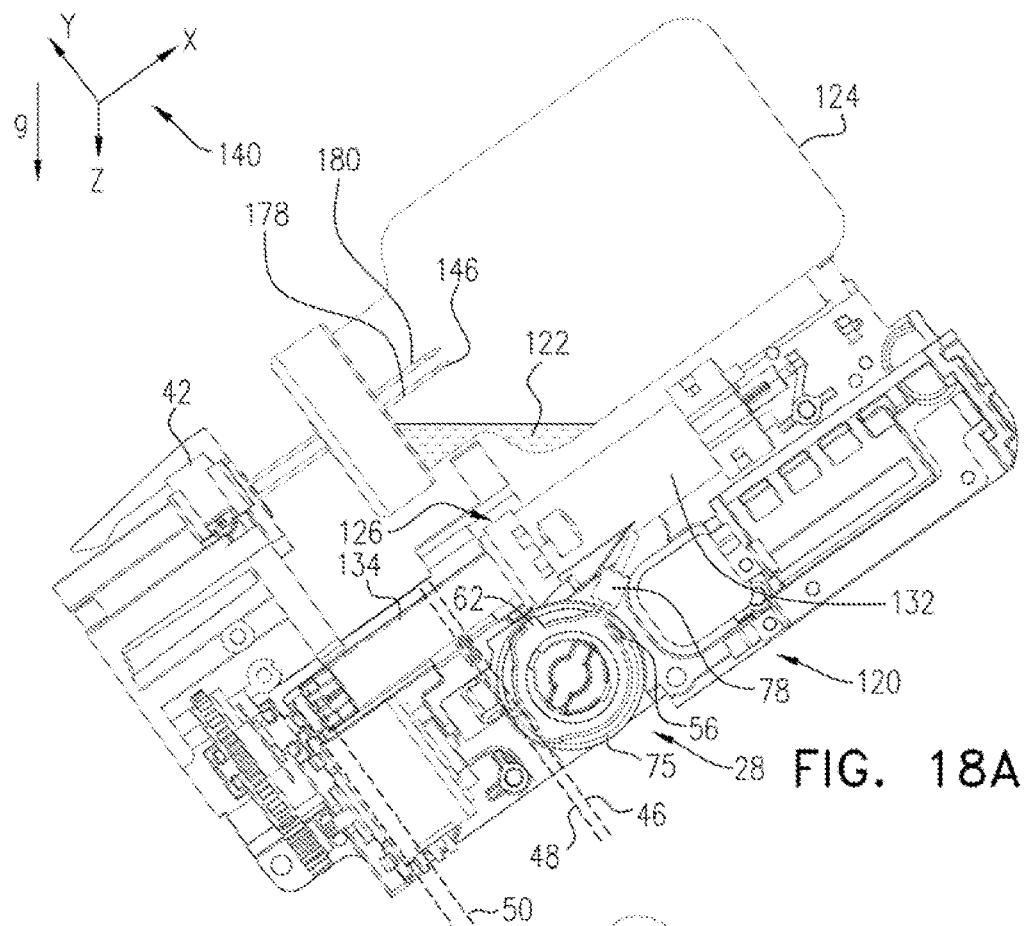
FIGS. 18A-B are schematic illustrations of different perspectives of the therapeutic substance delivery device of FIGS. 14A-B, showing a fourth motion phase of the plunger, in accordance with some applications of the present invention.
Figure 18B:
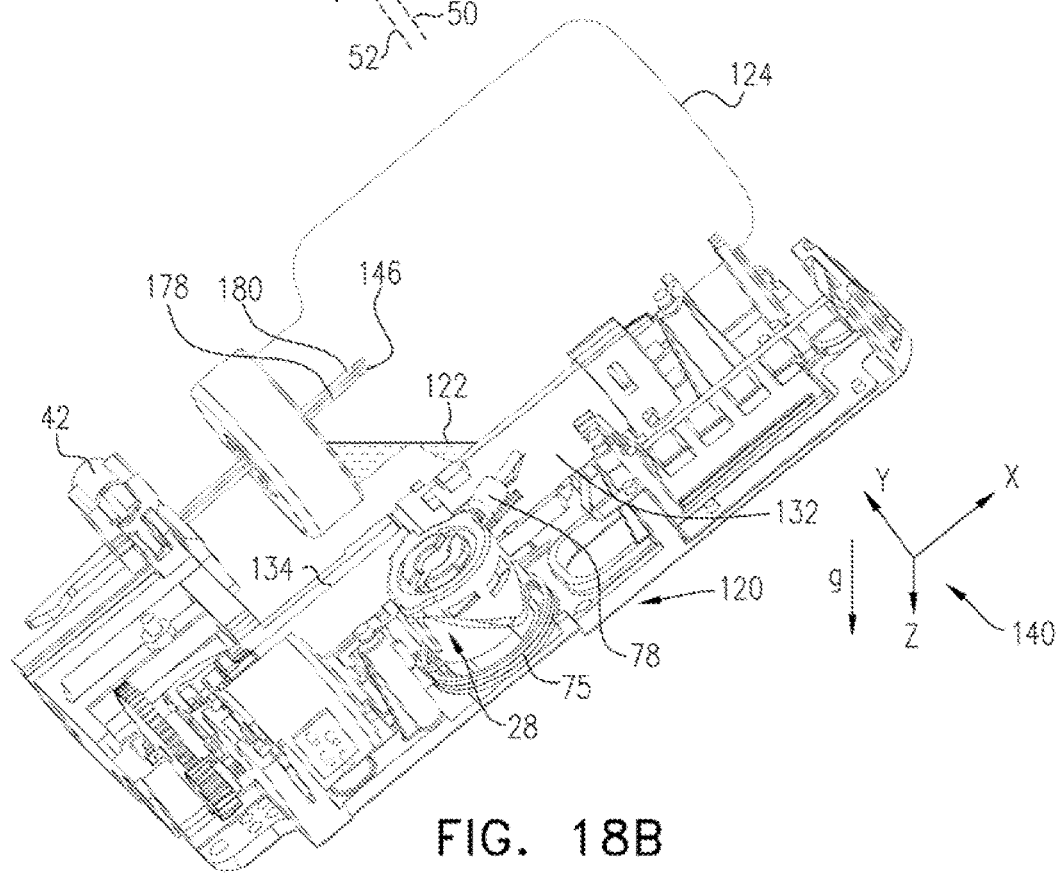

Reference is now made to FIGS. 18A-B, which are schematic illustrations of different perspectives of therapeutic substance delivery device 120 showing a fourth motion phase of plunger 134, in accordance with some applications of the present invention. Just as described hereinabove with reference to the second motion phase of plunger 36, typically, the fourth motion phase of plunger 134 is a maximal retraction of plunger 134 in the second direction, which causes body needle injection mechanism 28 to retract body needle 30 from the body of the subject, in the same manner as described hereinabove with reference to therapeutic substance delivery device 20. Dashed line 52 shows the stopping point for plunger 134 after plunger 134 performs the maximal retraction.

For some applications, the fourth motion phase of plunger 134 may be actuated once control circuitry 150 has determined that the treatment has ended, using the end of treatment detection method as described hereinabove with reference to FIG. 13. Once the volume of therapeutic substance 122 has been depleted to a point where regardless of the orientation of therapeutic substance delivery device 120, end 146 of reservoir needle 178 is not immersed in therapeutic substance 122, the reciprocating repetition of the second and third motion phases will cause air to be drawn through reservoir needle 178 into fluid intake path 128. In addition to this air helping to reduce dead volume by driving any remaining therapeutic substance 122 in the fluid path toward the subject, detection of this air may be used to determine that the treatment has ended and that body needle 30 should be removed from the body of the subject. As shown in FIGS. 18A-B, the volume of therapeutic substance 122 in reservoir 124 is substantially below end 146 of reservoir needle 178, plunger 134 has maximally retracted until dashed line 52, and body needle 30 has been retracted.

For some applications, such as for example when therapeutic substance reservoir 124 is replaceable, plunger 134, reservoir needle 178 and air needle 180 may be arranged such that the maximal retraction of plunger 134 retracts reservoir needle 178 and air needle 180 from therapeutic substance reservoir 124. For example, the maximal retraction of plunger 134 may cause rigid connecting element 44 to reconnect to plunger 134 and retract needle slider 42 as plunger 134 moves to a maximal retraction, which in turn retracts reservoir needle 178 and air needle 180.

Applications of the present invention may be combined with ultraviolet disinfection of:

(a) the engagement area between (i) therapeutic substance reservoir 124, and (ii) fluid intake path 128 and air path 136 (e.g., a septum of reservoir 124 that is pierced by fluid intake path 128 and air path 136 when therapeutic substance reservoir 124 is engaged with therapeutic substance delivery device 120), and/or (b) the engagement area between (i) therapeutic substance reservoir 22 and (ii) fluid path 26 (e.g., a septum of therapeutic substance reservoir 22 that is pierced by reservoir needle 24 of fluid path 26 when therapeutic substance reservoir 22 is engaged with therapeutic substance delivery device 20), using techniques described in US 2019/0134295 to Plaskin and in WO/2019/087198 to Ben-David, which are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for delivering a therapeutic substance to a subject, the apparatus comprising:

a therapeutic substance delivery device:

(a) configured to engage with a therapeutic substance reservoir, and (b) comprising a pump configured to draw the therapeutic substance from the reservoir into a pump chamber disposed within the therapeutic substance delivery device without changing internal dimensions of the reservoir, a volume of the therapeutic substance within the pump chamber varying in response to changes in internal dimensions of the pump chamber;

an orientation sensor coupled to the therapeutic substance delivery device and configured to generate an output indicative of an orientation of the therapeutic substance delivery device with respect to gravity; and control circuitry configured to drive the pump to:
  (a) calculate a volume of the therapeutic substance disposed within the reservoir,
  (b) drive the pump to draw the therapeutic substance into the pump chamber in response to (i) the calculated volume of the therapeutic substance disposed within the reservoir, in combination with (ii) an output from the orientation sensor that the therapeutic substance delivery device is in an orientation that allows the therapeutic substance to be drawn from the reservoir, and
  (c) drive the pump to deliver the therapeutic substance from the pump chamber to the subject.

2. The apparatus according to claim 1, wherein the therapeutic substance reservoir is a prefilled reservoir.

3. The apparatus according to claim 1, wherein the therapeutic substance reservoir is configured to be filled by the subject prior to engagement of the therapeutic substance reservoir with the therapeutic substance delivery device.

4. The apparatus according to claim 1, wherein the orientation sensor comprises an accelerometer.

5. The apparatus according to claim 1, wherein the control circuitry is configured to drive the pump to draw the therapeutic substance into the pump chamber substantially not in response to a predetermined therapeutic substance delivery schedule.

6. The apparatus according to claim 1, wherein the control circuitry is configured to drive the pump to interrupt the delivering of the therapeutic substance from the pump chamber to the subject by driving the pump to draw the therapeutic substance into the pump chamber from the therapeutic substance reservoir.

7. The apparatus according to claim 1, wherein the control circuitry is configured to drive the pump to draw the therapeutic substance into the pump chamber regardless of whether there is therapeutic substance within the pump chamber.

8. The apparatus according to claim 1, wherein:
  (A) the pump comprises:
    a fluid intake path, wherein the pump is configured to draw the therapeutic substance from the reservoir into the pump chamber via the fluid intake path,
    a fluid exit path, wherein the pump is configured to deliver the therapeutic substance from the pump chamber to the subject via the fluid exit path, and
    an air detector positioned to detect air within the fluid exit path, and
  (B) the control circuitry is configured to, in response to air being drawn into the pump chamber via the fluid intake path, calculate an amount of air detected within the fluid exit path.

9. The apparatus according to claim 8, wherein the control circuitry is configured to continue to drive the pump to deliver the therapeutic substance from the pump chamber to the subject in response to less than a threshold amount of air being detected in the fluid exit path.

10. The apparatus according to claim 8, wherein the control circuitry is configured such that, in response to more than a threshold amount of air being detected in the fluid exit path, the control circuitry performs a compensatory calculation to correct the calculated volume of therapeutic substance in the reservoir.

11. The apparatus according to claim 8, wherein the control circuitry is configured such that, in response to the amount of air detected in the fluid exit path passing an air-limit threshold, the control circuitry pauses the pump until an output from the orientation sensor is received that the therapeutic substance delivery device is in an orientation that allows the therapeutic substance to be drawn from the reservoir.

12. A method for delivering a therapeutic substance to a subject, the method comprising:
  using a therapeutic substance delivery device:
    drawing the therapeutic substance from a therapeutic substance reservoir into a pump chamber of the therapeutic delivery device, and
    delivering the therapeutic substance from the pump chamber to the subject,
    the drawing of the therapeutic substance being:
      (i) without changing internal dimensions of the reservoir, and
      (ii) substantially in response to (a) a volume of therapeutic substance in the reservoir, in combination with (b) an orientation of the therapeutic substance delivery device.

13. The method according to claim 12, wherein the drawing of the therapeutic substance is substantially not in response to a predetermined therapeutic substance delivery schedule.

14. The method according to claim 12, wherein drawing the therapeutic substance from the therapeutic substance reservoir comprises interrupting the delivering of the therapeutic substance from the pump chamber by filling the pump chamber with therapeutic substance from the therapeutic substance reservoir.

15. The method according to claim 12, wherein drawing the therapeutic substance from the reservoir comprises drawing the therapeutic substance from the reservoir regardless of whether there is therapeutic substance within the pump chamber.

16. The method according to claim 12, further comprising, using an orientation sensor, sensing the orientation of the therapeutic substance delivery device and generating an output indicative of the orientation of the therapeutic substance delivery device, and wherein drawing the therapeutic substance from the therapeutic substance reservoir into the pump chamber comprises drawing the therapeutic substance from the therapeutic substance reservoir substantially in response to (a) the volume of therapeutic substance in the reservoir, in combination with (b) the output from the orientation sensor.

17. The method according to claim 12, wherein:
  drawing the therapeutic substance comprises drawing the therapeutic substance from the therapeutic substance reservoir into the pump chamber via a fluid intake path,
  delivering the therapeutic substance from the pump chamber to the subject comprises delivering the therapeutic substance from the pump chamber via a fluid exit path, and
  the method further comprises, using an air detector, detecting that air has been drawn into the pump chamber by detecting air within the fluid exit path.

18. The method according to claim 17, further comprising:

using control circuitry, calculating an amount of air detected within the fluid exit path, and in response to less than a threshold amount of air being detected in the fluid exit path, continuing to deliver the therapeutic substance from the pump chamber to the subject.

19. The method according to claim 18, wherein, using the control circuitry, in response to more than the threshold amount of air being detected in the fluid path, performing a compensatory calculation to correct the calculated volume of therapeutic substance in the reservoir.

20. The method according to claim 17, further comprising:

using control circuitry, determining an amount of air detected within the fluid exit path, and in response to the amount of air detected in the fluid exit path passing an air-limit threshold, pausing the drawing until the orientation of the therapeutic substance delivery device is an orientation that allows the therapeutic substance to be drawn from the reservoir.

\* \* \* \* \*